US009926583B2

(12) United States Patent
Prentice et al.

(10) Patent No.: US 9,926,583 B2
(45) Date of Patent: *Mar. 27, 2018

(54) METHODS OF CELL CULTURE

(71) Applicant: Momenta Pharmaceuticals, Inc., Cambridge, MA (US)

(72) Inventors: Holly Prentice, Carlisle, MA (US); Rasheed Tijani, Haverhill, MA (US); Brett Belongia, North Andover, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/285,707

(22) Filed: Oct. 5, 2016

(65) Prior Publication Data

US 2017/0211114 A1 Jul. 27, 2017

Related U.S. Application Data

(63) Continuation of application No. 14/587,340, filed on Dec. 31, 2014, now Pat. No. 9,487,810, which is a continuation of application No. 13/829,292, filed on Mar. 14, 2013, now Pat. No. 8,956,830.

(51) Int. Cl.
*C12P 21/06* (2006.01)
*C12P 21/00* (2006.01)
*C12N 5/071* (2010.01)
*C12P 21/04* (2006.01)
*C12N 5/00* (2006.01)
*C12N 5/02* (2006.01)
*C12N 5/07* (2010.01)
*C12N 5/10* (2006.01)

(52) U.S. Cl.
CPC .......... *C12P 21/005* (2013.01); *C12N 5/0682* (2013.01); *C12N 2500/34* (2013.01); *C12N 2500/62* (2013.01); *C12N 2510/02* (2013.01)

(58) Field of Classification Search
None
See application file for complete search history.

(56) References Cited

U.S. PATENT DOCUMENTS

| RE30,985 E | 6/1982 | Cartaya |
| 5,063,157 A | 11/1991 | Stockinger |
| 5,122,469 A | 6/1992 | Mather et al. |
| 5,426,699 A | 6/1995 | Wunderlich et al. |
| 5,804,420 A | 9/1998 | Chan et al. |
| 5,811,299 A | 9/1998 | Renner et al. |
| 6,528,286 B1 | 3/2003 | Ryll |
| 6,673,575 B1 | 1/2004 | Franze et al. |
| 8,956,830 B2 | 2/2015 | Prentice et al. |
| 9,217,168 B2 | 12/2015 | Prentice |
| 9,487,810 B2 | 11/2016 | Prentice et al. |
| 9,663,810 B2 * | 5/2017 | Prentice ................ C12P 21/005 |
| 9,677,105 B2 * | 6/2017 | Collins ................ C12P 21/02 |
| 2009/0068705 A1 | 3/2009 | Drapeau et al. |
| 2009/0214528 A1 | 8/2009 | Dorai et al. |
| 2010/0113294 A1 | 5/2010 | Venkataraman et al. |
| 2010/0137195 A1 | 6/2010 | Weber et al. |
| 2010/0221823 A1 | 9/2010 | McCoy et al. |
| 2012/0035110 A1 | 2/2012 | Grillberger et al. |
| 2012/0164137 A1 | 6/2012 | Sass et al. |
| 2012/0183997 A1 | 7/2012 | Alley et al. |
| 2012/0295273 A1 | 11/2012 | Washburn et al. |

FOREIGN PATENT DOCUMENTS

| WO | WO-00/65070 A2 | 11/2000 |
| WO | WO-2005/028626 A2 | 3/2005 |
| WO | WO-2008/154014 A2 | 12/2008 |
| WO | WO-2010/141855 A1 | 12/2010 |
| WO | WO-2011/061275 A1 | 5/2011 |
| WO | WO-2011/119115 A1 | 9/2011 |
| WO | WO-2011/127322 A1 | 10/2011 |

OTHER PUBLICATIONS

Andersen, D. C. et al., The Effect of Ammonia on the O-Linked Glycosylation of Granulocyte Colony-Stimulating Factor Produced by Chinese Hamster Ovary Cells, Biotechnology and Bioengineering, 47:96-105 (1995).
Bioli-N'Garagba, M. C. et al., Polyamine Participation in the Maturation of Glycoprotein Fucosylation, but not Sialylation, in Rat Small Intestine, Pediatric Research, 51(5):625-634 (2002).
Borys, M. C. et al., Ammonia Affects the Glycosylation Patterns of Recombinant Mouse Placental Lactogen-I by Chinese Hamster Ovary Cells in a pH-Dependent Manner, Biotechnology and Bioengineering, 43:505-514 (1994).
Camakaris, J., et al., Gene Amplification of the Menkes (MNK; ATP7A) P-type ATPase Gene of CHO Cells is Associated with Copper Resistance and Enhanced Copper Efflux, Human Molecular Genetics, 4(11):2117-2123 (1995).
Chaderjian, W. B. et al., Effect of Copper Sulfate on Performance of a Serum-Free CHO Cell Culture Process and the Level of Free Thiol in the Recombinant Antibody Expressed, Biotechnology Progress, 21:550-553 (2005).
Chen, P. et al., Effects of Elevated Ammonium on Glycosylation Gene Expression in CHO Cells, Metabolic Engineering, 8:123-0132 (2006).
Cooper, C. A. et al., GlycoSuiteDB: A Curated Relational Database of Glycoprotein Glycan Structures and Their Biological Sources. 2003 Update, Nucleic Acids Research, 31(1):511-513 (2003).
Cox, K. M. et al., Glycan Optimization of a Human Monoclonal Antibody in the Aquatic Plant *Lemna Minor*, Nature Biotechnology, 24(12):1591-1597 (2006).

(Continued)

Primary Examiner — Nancy J Leith

(74) Attorney, Agent, or Firm — Choate, Hall & Stewart LLP; Brenda Herschbach Jarrell; Rolando Medina

(57) ABSTRACT

Polypeptide preparations having target levels of glycans, and methods of producing such polypeptide preparations using DMSO, are described.

36 Claims, 6 Drawing Sheets

(56) References Cited

OTHER PUBLICATIONS

Crowell, C. K. et al., Amino Acid and Manganese Supplementation Modulates the Glycosylation State of Erythropoietin in a CHO Culture System, Biotechnology and Bioengineering, 96(3):538-549, 2007.

Eisses, J. F. et al., Molecular Characterization of hCTR1, the Human Copper Uptake Protein, The Journal of Biological Chemistry, 277(32):29162-29171 (2002).

Gawlitzek, M. et al., Ammonium Alters N-Glycan Structures of Recombinant TNFR-IgG: Degradative Versus Biosynthetic Mechanisms, Biotechnology and Bioengineering, 68(6):637-646 (2000).

Gawlitzek, M. et al., Ammonium Ion and Glucosamine Dependent Increases of Oligosaccharide Complexity in Recombinant Glycoproteins Secreted from Cultivated BHK-21 Cells, Biotechnology and Bioengineering, 57(5):518-528 (1998).

Gawlitzek, M. et al., Characterization of Changes in the Glycosylation Pattern of Recombinant Proteins from BHK-21 Cells Due to Different Culture Conditions, Journal of Biotechnology, 42:117-131 (1995).

Goetze, A.M. et al., High-mannose glycans on the Fc region of therapeutic IgG antibodies increase serum clearance in humans, Glycobiology, 21(7):949-959 (2011).

Gouveia, R., et al., Production and N-glycosylation of Recombinant Human Cell Adhesion Molecule L1 from Insect Cells Using the Stable Expression System. Effect of Dimethyl Sulfoxide, Journal of Biotechnology, 145:130-138 (2010).

Grammatikos, S. I., et al., Intracellular UDP-N-Acetylhexosamine Pool Affects N-Glycan Complexity: A Mechanism of Ammonium Action on Protein Glycosylation, Biotechnol. Prog., 14:410-419 (1998).

Greco, S. et al., Influence of spermine on intestinal maturation of the glycoprotein glycosylation process in neonatal rats, Biochemical Journal, 345:69-75 (2000).

Gréco, S., et al., Dietary Spermidine and Spermine Participate in the Maturation of Galactosyltransferase Activity and Glycoprotein Galactosylation in Rat Small Intestine, Journal of Nutrition, 131(7):1890-1897 (2001).

Hendrick, V., et al., Increased Productivity of Recombinant Tissular Plasminogen Activator (t-PA) by Butyrate and Shift of Temperature: A Cell Cycle Phases Analysis, Cytotechnology, 36:71-83 (2001).

Hirschberg, C B., Transporters of Nucleotide Sugars, Nucleotide Sulfate and ATP in the Golgi Apparatus Membrane: Where Next?, Glycobiology, 7(2):169-171 (1997).

Hosoi, S., et al., Modulation of Oligosaccharide Structure of a Pro-Urokinase Derivative (Pro-UKΔGS1) by Changing Culture Conditions of a Lymphoblastoid Cell Line Namalwa KJM-1 Adapted to Serum-Free Medium, Cytotechnology, 19:125-135 (1996).

Hossler, P., et al., Optimal and Consistent Protein Glycosylation in Mammalian Cell Culture, Glycobiology, 19(9):936-949 (2009).

Hultberg, B., et al., Copper Ions Differ from Other Thiol Reactive Metal Ions in Their Effects on the Concentration and Redox Status of Thiols in HeLa Cell Cultures, Toxicology, 117:89-97 (1997).

Igarashi, K. and Kashiwagi, K., Modulation of cellular function by polyamines, The International Journal of Biochemistry & Cell Biology, 42:39-51 (2010).

Iizuka, M. et al., Production of a recombinant mouse monoclonal antibody in transgenic silkworm cocoons, FEBS Journal, 276:5806-5820 (2009).

International Search Report for PCT/US14/23900, 5 pages (dated Sep. 10, 2014).

International Search Report for PCT/US2014/023892, dated Jun. 3, 2014 (4 pages).

International Search Report for PCT/US2014/023917, dated Jun. 13, 2014 (3 pages).

International Search Report for PCT/US2014/023924, dated Jun. 27, 2014 (3 pages).

Jefferis, Roy, Glycosylation as a strategy to improve antibody-based therapeutics, Nature Review, Drug Discovery, 8:225-234 (2009).

Jefferis, Roy, Glycosylation of Recombinant Antibody Therapeutics, Biotechnol. Prog., 21:11-16 (2005).

Joosten, C. E., et al., Effect of Culture Conditions on the Degree of Sialylation of a Recombinant Glycoprotein Expressed in Insect Cells, Biotechnology Progress, 19:739-749 (2003).

Kaschak, T., et al., Characterization of the Basic Charge Variants of a Human IgG1: Effect of Copper Concentration in Cell Culture Media, mAbs, 3(6):577-583 (2011).

Kim, Y. K., et al., Production and N-Glycan Analysis of Secreted Human Erythropoietin Glycoprotein in Stably Transfected *Drosophila* S2 Cells, Biotechnology and Bioengineering, 92(4):452-461 (2005).

Lifely, M. R., et al., Glycosylation and Biological Activity of CAMPATH-1H Expressed in Different Cell Lines and Grown Under Different Culture Conditions, Glycobiology, 5(8):813-822 (1995).

Ling, W. and Deng, L., Dimethyl Sulfoxide-Induced Stimulation on Monoclonal Antibody Production is Regulated by p39 Mitogen-Activated Protein Kinase in Hybridoma Cells, Monoclonal Antibodies: New Research, pp. 143-150 (2005).

Liu, C. and Chen, L., Promotion of Recombinant Macrophage Colony Stimulating Factor Production by Dimethyl Sulfoxide Addition in Chinese Hamster Ovary Cells, Journal of Bioscience and Bioengineering, 103(I):45-49 (2007).

Luo, J., et al., Probing of C-Terminal Lysine Variation in a Recombinant Monoclonal Antibody Production Using Chinese Hamster Ovary Cells With Chemically Defined Media, Biotechnology and Bioengineering, 109(9):2306-2315 (2012).

Martinelle, K., et al., Mechanisms of Ammonia and Ammonium Ion Toxicity in Animal Cells: Transport Across Cell Membranes, Journal of Biotechnology, 30:339-350 (1993).

McQueen, A., et al., Effect of Ammonium Ion and Extracellular pH on Hybridoma Cell Metabolism and Antibody Production, Biotechnology and Bioengineering, 35:1067-1077 (1990).

Nam, J. H., et al., The Effects of Culture Conditions on the Glycosylation of Secreted Human Placental Alkaline Phosphatase Produced in Chinese Hamster Ovary Cells, Biotechnology and Bioengineering, 100(6):1178-1192 (2008).

O'Donovan, E., et al., Process Improvements for Production of a Complex Glycosylated Fusion Protein which Delivers a Two-Fold Increase in Product Titre and Comparable Product Quality, ESACT Proceedings, 5:429-431 (2012).

Qian, Y., et al., Cell Culture and Gene Transcription Effects of Copper Sulfate on Chinese Hamster Ovary Cells, Biotechnol. Prog., 27(4):1190-1194 (2011).

Robinson, D. K., et al., Characterization of a Recombinant Antibody Produced in the Course of a High Yield Fed-Batch Process, Biotechnology and Bioengineering, 44:727-735 (1994).

Rodriguez, J., et al., Enhanced Production of Monomeric Interferon-β by CHO Cells through the Control of Culture Conditions, Biotechnol. Prog., 21:22-30 (2005).

Ryll, T., Biochemistry of Growth Inhibition by Ammonium Ions in Mammalian Cells, Biotechnology and Bioengineering, 44:184-193 (1994).

Staudacher, E. et al., Functional purification and characterization of a GDP-fucose: β-N-acetylglucosamine (Fuc to Asn linked GlcNAc) α1,3-fucosyltransferase from mung beans, Glycoconjugate Journal, 12:780-786 (1995).

Thorens, B., et al., Chloroquine and Ammonium Chloride Prevent Terminal Glycosylation of Immunoglobulins in Plasma Cells without Affecting Secretion, Nature, 321:618-620 (1986).

Valley, U., et al., Incorporation of Ammonium into Intracellular UDP-Activated N-Acetylhexosamines and into Carbohydrate Structures in Glycoproteins, Biotechnology and Bioengineering, 64(4):401-417 (1999).

Witsell, D. L. et al., Divalent Cation Activation of Galactosyltransferase in Native Mammary Golgi Vesicles, Journal of Biological Chemistry, 265(26):15731-15737 (1990).

Written Opinion for PCT/US2014/023892, dated Jun. 3, 2014 (9 pages).

Written Opinion for PCT/US2014/023900, 15 pages (dated Sep. 10, 2014).

Written Opinion for PCT/US2014/023917, dated Jun. 13, 2014 (9 pages).

(56) References Cited

OTHER PUBLICATIONS

Written Opinion for PCT/US2014/023924, dated Jun. 27, 2014 (10 pages).
Yang, M., et al., Effect of Ammonia on the Glycosylation of Human Recombinant Erythropoietin in Culture, Biotechnol. Prog., 16:751-759 (2000).
Yang, M., et al., Effects of Ammonia and Glucosamine on the Heterogeneity of Erythropoietin Glycoforms, Biotechnol. Prog., 18:129-138 (2002).
Yang, M., et al., Effects of Ammonia on CHO Cell Growth, Erythropoietin Production, and Glycosylation, Biotechnology and Bioengineering, 68(4): 370-380 (2000).

\* cited by examiner 3,3,1,0,0 Complex 3,5,1,1,0 Sialylated

METHODS OF CELL CULTURE

CROSS REFERENCE TO RELATED APPLICATIONS

The present application is a continuation of U.S. application Ser. No. 14/587,340, filed Dec. 31, 2014, which is a continuation of U.S. application Ser. No. 13/829,292, filed Mar. 14, 2013 now U.S. Pat. No. 8,956,830, the contents of all of which are herein incorporated by reference in their entirety

FIELD OF THE INVENTION

The invention relates generally to cell culture methods.

BACKGROUND

Therapeutic polypeptides are an important class of therapeutic biotechnology products, and therapeutic antibodies (including murine, chimeric, humanized and human antibodies and fragments thereof) account for the majority of therapeutic biologic products.

SUMMARY

In one aspect, the invention features a method of producing a recombinant protein preparation having a target value of one or more of high mannose glycans and fucosylated glycans, the method comprising: (a) providing a cell genetically engineered to express a recombinant protein; (b) culturing the cell in a culture medium comprising (e.g., supplemented with) DMSO under conditions in which the cell expresses the recombinant protein; and (c) harvesting (e.g., purifying or isolating from the cell and/or culture medium) a preparation of the recombinant protein produced by the cell, wherein the preparation has the target value of the one or more of high mannose glycans and fucosylated glycans. In some embodiments, the culture medium comprises DMSO for a time and in an amount effective to modify (e.g., increase or decrease) one or more of the high mannose glycans and fucosylated glycans of the recombinant protein.

In some embodiments, the culture medium comprises at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%. 4.5%, 4.6%, 4.7%, 4.8%, 4.9%, or 5% DMSO. In some embodiments, the culture medium comprises about 0.1% to 5% DMSO, about 0.1% to about 1% DMSO, about 1% to about 2% DMSO, about 2% to about 3% DMSO, about 3% to about 4% DMSO, about 4% to about 5% DMSO, about 0.1% to about 2.5% DMSO, about 2.5% to about 5% DMSO, about 0.1% to about 2% DMSO, about 0.1% to about 3% DMSO, about 0.1% to about 4% DMSO, about 1% to about 5% DMSO, about 2% to about 5% DMSO, or about 3% to about 5% DMSO.

In some embodiments, the target value is a level of one or more of high mannose glycans and fucosylated glycans in a reference therapeutic product. In some embodiments, the target value is a level of one or more of high mannose glycans and fucosylated glycans in a reference therapeutic antibody product. In some embodiments, the target value is a predetermined pharmaceutical product specification or a quality control criterion for a pharmaceutical preparation, e.g., a Certificate of Analysis (CofA), a Certificate of Testing (CofT), or a Master Batch Record. In some embodiments, the product specification is a product description in an FDA label, a Physician's Insert, a USP monograph, or an EP monograph.

In some embodiments, the reference therapeutic product is selected from the group consisting of: abatacept, abciximab, adalimumab, aflibercept, alefacept, alemtuzumab, basiliximab, bevacizumab, belatacept, certolizumab, cetuximab, daclizumab, eculizumab, efalizumab, entanercept, gemtuzumab, ibritumomab, infliximab, muromonab-CD3, natalizumab, omalizumab, palivizumab; panitumumab, ranibizumab, rilonacept, rituximab, tositumomab, and trastuzumab.

In some embodiments, the target value is one or more of: (a) at least about 0.1% to about 20% high mannose glycans, e.g., at least about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, or more, high mannose glycans; and (b) at least about 70% to 100% fucosylated glycans, e.g., at least about 70%, about 75%, about 80%, about 85%, about 90%, about 95%, or about 100% fucosylated glycans. High mannose glycans can be, e.g., HM3, HM4, HM5, HM6, HM7, HM8, HM9, or combinations thereof.

In some embodiments, the target value of the one or more of high mannose glycans and fucosylated glycans is higher than a corresponding level in a preparation produced by culturing the cell in the medium not comprising DMSO. In some embodiments, the target value is higher than the corresponding level by at least about 10%, 20%, 30%, 40%, 50%, 60%, 70%, 80%, 90%, 100%, 150%, 200%, 250%, 300%, 350%, 400%, 450%, 500%, or more, of the corresponding level.

In some embodiments, the method further comprises evaluating the level of one or more of high mannose glycans and fucosylated glycans in the recombinant protein preparation. In some embodiments, the method further comprises recording the level in a print or computer-readable medium, e.g., in a test report, Material Safety Data Sheet (MSDS), batch record, Certificate of Testing (CofT) or Certificate of Analysis (CofA).

In another aspect, the invention features a method of producing a recombinant protein preparation, the method comprising: (a) providing a target value of one or more of high mannose glycans and fucosylated glycans; (b) providing a cell genetically engineered to express a recombinant protein; (c) culturing the cell in a culture medium comprising (e.g., supplemented with) DMSO under conditions in which the cell expresses the recombinant protein; (d) harvesting a preparation of the recombinant protein produced by the cell; and (e) processing (e.g., one or more of formulating, filling into a container, labeling, packaging) the preparation into a drug product if the preparation meets the target value of the one or more of high mannose glycans and fucosylated glycans. In some embodiments, the culture medium comprises DMSO for a time and in an amount effective to modify (e.g., increase or decrease) one or more of the high mannose glycans and fucosylated glycans of the recombinant protein.

In some embodiments, the method further comprises evaluating the level of one or more of high mannose glycans and fucosylated glycans in the recombinant protein preparation. In some embodiments, the method further comprises recording the level in a print or computer-readable medium, e.g., in a test report, Material Safety Data Sheet (MSDS), batch record, or Certificate of Testing (CofT) or Certificate of Analysis (CofA).

In some embodiments, the culture medium comprises at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%. 4.5%, 4.6%, 4.7%, 4.8%, 4.9%, or 5% DMSO. In some embodiments, the culture medium comprises about 0.1% to 5% DMSO, about 0.1% to about 1% DMSO, about 1% to about 2% DMSO, about 2% to about 3% DMSO, about 3% to about 4% DMSO, about 4% to about 5% DMSO, about 0.1% to about 2.5% DMSO, about 2.5% to about 5% DMSO, about 0.1% to about 2% DMSO, about 0.1% to about 3% DMSO, about 0.1% to about 4% DMSO, about 1% to about 5% DMSO, about 2% to about 5% DMSO, or about 3% to about 5% DMSO.

In some embodiments, the target value is a level of one or more of high mannose glycans and fucosylated glycans in a reference therapeutic product. In some embodiments, the target value is a level of one or more of high mannose glycans and fucosylated glycans in a reference therapeutic antibody product. In some embodiments, the target value is a predetermined pharmaceutical product specification or a quality control criterion for a pharmaceutical preparation, e.g., a Certificate of Analysis (CofA), a Certificate of Testing (CofT), or a Master Batch Record. In some embodiments, the product specification is a product description in an FDA label, a Physician's Insert, a USP monograph, or an EP monograph.

In some embodiments, the reference therapeutic product is selected from the group consisting of: abatacept, abciximab, adalimumab, aflibercept, alefacept, alemtuzumab, basiliximab, bevacizumab, belatacept, certolizumab, cetuximab, daclizumab, eculizumab, efalizumab, entanercept, gemtuzumab, ibritumomab, infliximab, muromonab-CD3, natalizumab, omalizumab, palivizumab; panitumumab, ranibizumab, rilonacept, rituximab, tositumomab, and trastuzumab.

In some embodiments, the target value is one or more of: (a) at least about 0.1% to about 20% high mannose glycans, e.g., at least about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, or more, high mannose glycans; and (b) at least about 70% to 100% fucosylated glycans, e.g., at least about 70%, about 75%, about 80%, about 85%, about 90%, about 95%, or about 100% fucosylated glycans. High mannose glycans can be, e.g., HM3, HM4, HM5, HM6, HM7, HM8, HM9, or combinations thereof.

In some embodiments, the target value of the one or more of high mannose glycans and fucosylated glycans is higher than a corresponding level in a preparation produced by culturing the cell in the medium not comprising DMSO. In some embodiments, the target value is higher than the corresponding level by at least about 10%, 20%, 30%, 40%, 50%, 60%, 70%, 80%, 90%, 100%, 150%, 200%, 250%, 300%, 350%, 400%, 450%, 500%, or more, of the corresponding level.

In another aspect, the invention features a method of increasing a level of one or more of high mannose glycans, sialylated glycans, and 3,3,1,0,0 glycans in a recombinant protein preparation, the method comprising: (a) providing a cell genetically engineered to express a recombinant protein; (b) culturing the cell in a culture medium comprising (e.g., supplemented with) DMSO under conditions in which the cell expresses the recombinant protein; and (c) harvesting a preparation of the recombinant protein produced by the cell, wherein the preparation has an increased level of one or more of high mannose glycans, sialylated glycans, and 3,3,1,0,0 glycans relative to a corresponding level in a preparation of the recombinant protein produced by culturing the cell in the medium not comprising DMSO. In some embodiments, the culture medium comprises DMSO for a time and in an amount effective to increase one or more of the high mannose glycans, sialylated glycans, and 3,3,1,0,0 glycans of the recombinant protein. In some embodiments, the method further comprises processing, (e.g., one or more of formulating, filling into a container, labeling, packaging) the preparation into a drug product if the preparation meets a target value of one or more of high mannose glycans, sialylated glycans, and 3,3,1,0,0 glycans.

In some embodiments, the culture medium comprises at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%. 4.5%, 4.6%, 4.7%, 4.8%, 4.9%, or 5% DMSO. In some embodiments, the culture medium comprises about 0.1% to 5% DMSO, about 0.1% to about 1% DMSO, about 1% to about 2% DMSO, about 2% to about 3% DMSO, about 3% to about 4% DMSO, about 4% to about 5% DMSO, about 0.1% to about 2.5% DMSO, about 2.5% to about 5% DMSO, about 0.1% to about 2% DMSO, about 0.1% to about 3% DMSO, about 0.1% to about 4% DMSO, about 1% to about 5% DMSO, about 2% to about 5% DMSO, or about 3% to about 5% DMSO.

In some embodiments, the method further comprises measuring a level of the one or more of high mannose glycans, sialylated glycans, and 3,3,1,0,0 glycans in the recombinant protein preparation. In some embodiments, the method further comprises recording the level in a print or computer-readable medium, e.g., in a test report, Material Safety Data Sheet (MSDS), batch record, Certificate of Testing (CofT) or Certificate of Analysis (CofA).

In some embodiments, the increased level of the one or more of high mannose glycans, sialylated glycans, and 3,3,1,0,0 glycans is higher than the corresponding level by at least about 10%, 20%, 30%, 40%, 50%, 60%, 70%, 80%, 90%, 100%, 150%, 200%, 250%, 300%, 350%, 400%, 450%, 500%, or more, of the corresponding level. In some embodiments, the increased level is one or more of: (a) at least about 0.1% to about 20% high mannose glycans, e.g., at least about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, or more, high mannose glycans; (b) at least about 70% to 100% fucosylated glycans, e.g., at least about 70%, about 75%, about 80%, about 85%, about 90%, about 95%, or about 100% fucosylated glycans; and (c) at least about 0.1% to about 90% sialylated glycans, e.g., at least about 20%, 30%, 40%, 50%, 60%, 70%, 80%, or 90% sialylated glycans. High mannose glycans can be, e.g., HM3, HM4, HM5, HM6, HM7, HM8, HM9, or combinations thereof.

In another aspect, the invention features a method of decreasing a level of one or more of high mannose glycans, sialylated glycans, and 3,3,1,0,0 glycans in a recombinant protein preparation, the method comprising: (a) providing a cell genetically engineered to express a recombinant protein; (b) culturing the cell in a culture medium comprising a reduced level of DMSO under conditions in which the cell expresses the recombinant protein; and (c) harvesting a preparation of the recombinant protein produced by the cell, wherein the preparation has a decreased level of one or more of high mannose glycans, sialylated glycans, and 3,3,1,0,0 glycans relative to a corresponding level in a preparation of the recombinant protein produced by culturing the cell in the medium not comprising the reduced level of DMSO. In some embodiments, the culture medium comprises the reduced level of DMSO for a time and in an amount effective to decrease a level of one or more of the high mannose glycans, sialylated glycans, and 3,3,1,0,0 glycans of the recombinant protein. In some embodiments, the method further comprises processing, (e.g., one or more of formulating, filling into a container, labeling, packaging) the preparation into a drug product if the preparation meets a target value of one or more of high mannose glycans, sialylated glycans, and 3,3,1,0,0 glycans.

In some embodiments, the medium comprises less than about 5%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1%; or 0% DMSO.

In some embodiments, the method further comprises measuring a level of the one or more of high mannose glycans, sialylated glycans, and 3,3,1,0,0 glycans in the recombinant protein preparation. In some embodiments, the method further comprises recording the level in a print or computer-readable medium, e.g., in a test report, Material Safety Data Sheet (MSDS), batch record, Certificate of Testing (CofT) or Certificate of Analysis (CofA).

In some embodiments, the decreased level of the one or more of high mannose glycans, sialylated glycans, and 3,3,1,0,0 glycans is lower than the corresponding level by at least about 10%, 20%, 30%, 40%, 50%, 60%, 70%, 80%, 90%, 95%, or 100%, of the corresponding level. In some embodiments, the decreased level is one or more of: (a) less than about 20% high mannose glycans; (b) less than about 90% fucosylated glycans; and (c) less than about 90% sialylated glycans. High mannose glycans can be, e.g., HM3, HM4, HM5, HM6, HM7, HM8, HM9, or combinations thereof.

In another aspect, the invention features a method of decreasing a level of one or more fucosylated glycans in a recombinant protein preparation, the method comprising: (a) providing a cell genetically engineered to express a recombinant protein; (b) culturing the cell in a culture medium comprising (e.g., supplemented with) DMSO under conditions in which the cell expresses the recombinant protein; and (c) harvesting a preparation of the recombinant protein produced by the cell, wherein the preparation has a decreased level of one or more fucosylated glycans relative to a corresponding level in a preparation of the recombinant protein produced by culturing the cell in the medium not comprising DMSO. In some embodiments, the culture medium comprises DMSO for a time and in an amount effective to decrease the level of one or more fucosylated glycans of the recombinant protein. In some embodiments, the method further comprises processing, (e.g., one or more of formulating, filling into a container, labeling, packaging) the preparation into a drug product if the preparation meets a target value of one or more fucosylated glycans.

In some embodiments, the culture medium comprises at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% DMSO. In some embodiments, the culture medium comprises about 0.1% to 5% DMSO, about 0.1% to about 1% DMSO, about 1% to about 2% DMSO, about 2% to about 3% DMSO, about 3% to about 4% DMSO, about 4% to about 5% DMSO, about 0.1% to about 2.5% DMSO, about 2.5% to about 5% DMSO, about 0.1% to about 2% DMSO, about 0.1% to about 3% DMSO, about 0.1% to about 4% DMSO, about 1% to about 5% DMSO, about 2% to about 5% DMSO, or about 3% to about 5% DMSO.

In some embodiments, the method further comprises measuring a level of fucosylated glycans in the recombinant protein preparation. In some embodiments, the method further comprises recording the level in a print or computer-readable medium, e.g., in a test report, Material Safety Data Sheet (MSDS), batch record, Certificate of Testing (CofT) or Certificate of Analysis (CofA).

In some embodiments, the decreased level of the fucosylated glycans is lower than the corresponding level by at least about 10%, 20%, 30%, 40%, 50%, 60%, 70%, 80%, 90%, 95%, or 100%, of the corresponding level. In some embodiments, the decreased level is less than about 100% fucosylated glycans. In some embodiments, the one or more fucosylated glycans comprise G0F glycans.

In another aspect, the invention features a method of increasing a level of one or more fucosylated glycans in a recombinant protein preparation, the method comprising: (a) providing a cell genetically engineered to express a recombinant protein; (b) culturing the cell in a culture medium comprising a reduced level of DMSO under conditions in which the cell expresses the recombinant protein; and (c) harvesting a preparation of the recombinant protein produced by the cell, wherein the preparation has an increased level of one or more fucosylated glycans relative to a corresponding level in a preparation of the recombinant protein produced by culturing the cell in the medium not comprising the reduced level of DMSO. In some embodiments, the culture medium comprises a reduced level of DMSO for a time and in an amount effective to increase the level of one or more fucosylated glycans of the recombinant protein. In some embodiments, the method further comprises processing, (e.g., one or more of formulating, filling into a container, labeling, packaging) the preparation into a drug product if the preparation meets a target value of one or more fucosylated glycans.

In some embodiments, the medium comprises less than about 5%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1%; or 0% DMSO.

In some embodiments, the method further comprises measuring a level of fucosylated glycans in the recombinant protein preparation. In some embodiments, the method further comprises recording the level in a print or computer-readable medium, e.g., in a test report, Material Safety Data Sheet (MSDS), batch record, Certificate of Testing (CofT) or Certificate of Analysis (CofA).

In some embodiments, the increased level of the fucosylated glycans is higher than the corresponding level by at least about 10%, 20%, 30%, 40%, 50%, 60%, 70%, 80%, 90%, 100%, 150%, 200%, 250%, 300%, 350%, 400%, 450%, 500%, or more, of the corresponding level. In some embodiments, the increased level is at least about 70% to 100% fucosylated glycans, e.g., at least about 70%, about 75%, about 80%, about 85%, about 90%, about 95%, or about 100% fucosylated glycans. In some embodiments, the one or more fucosylated glycans comprise G0F glycans.

In some aspects described herein, the culturing step comprises a first stage and a second stage. In some embodiments, the first stage comprises culturing the cell in a first culture medium comprising a first level of DMSO, and the second stage comprises culturing the cell in a second culture medium comprising a second level of DMSO. In some embodiments, the first culture medium comprises a reduced level of (e.g., does not comprise) DMSO relative to the second culture medium and the second culture medium comprises an elevated level of DMSO (e.g., about 1% to about 5% DMSO) relative to the first culture medium. In some embodiments, the first culture medium comprises an elevated level of DMSO (e.g., about 1% to about 5% DMSO), and the second culture medium comprises a reduced level of (e.g., does not comprise) DMSO.

In some embodiments, the first stage comprises culturing the cell in the first culture medium for about 1 to about 8 days, e.g., 1-7, 1-6, 1-5 days. In some embodiments, the second stage comprises culturing the cell in the second culture medium for about 1 to about 12 days, e.g., 1-10, 1-9, 1-8, 1-7, 1-6 days. In some embodiments, the first stage is a growth stage. In some embodiments, the second stage is a production stage.

In some aspects described herein, the culture medium further comprises one or more of lysine, cysteine, ammonium, manganese, copper, cobalt, putrescine, a peptone, glucose, galactose, glucosamine, glutamine, a lipid (e.g., cholesterol), and dextran sulfate.

In some aspects described herein, the cell is a mammalian cell. In some embodiments, the mammalian cell is a CHO (e.g., CHO-K1, DG44, CHO-DXB11, CHOK1SV, CHO-S) Vero, BHK, HeLa, COS, MDCK, or HEK-293 cell.

In some aspects described herein, the recombinant protein is a recombinant therapeutic product. In some embodiments, the recombinant protein is a recombinant therapeutic antibody product. In some embodiments, the recombinant protein is a recombinant therapeutic fusion protein. In some embodiments, the recombinant protein is abatacept, abciximab, adalimumab, aflibercept, alefacept, alemtuzumab, basiliximab, bevacizumab, belatacept, certolizumab, cetuximab, daclizumab, eculizumab, efalizumab, entanercept, gemtuzumab, ibritumomab, infliximab, muromonab-CD3, natalizumab, omalizumab, palivizumab; panitumumab, ranibizumab, rilonacept, rituximab, tositumomab, and trastuzumab.

In some aspects described herein, the conditions in which cells (e.g., mammalian cells) express recombinant proteins comprise (i) a medium having a pH of about 6, about 6.5, about 6.6, about 6.7, about 6.8, about 6.9, about 7, about 7.1, about 7.2, about 7.3, about 7.4, about 7.5, or about 8; (ii) a temperature of about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C.; and/or (iii) a culture volume of about 100 mL, about 200 mL, about 300 mL, about 400 mL, about 500 mL, about 600 mL, about 700 mL, about 800 mL, about 900 mL, about 1 L, about 2 L, about 3 L, about 5 L, about 10 L, about 20 L, about 30 L, about 40 L, about 50 L, about 100 L, about 200 L, about 300 L, about 400 L, about 500 L, about 600 L, about 700 L, about 800 L, about 900 L, about 1000 L, 5,000 L, 10,000 L, 20,000 L, or more.

In another aspect, the invention features a preparation of a recombinant protein produced using a method described herein.

In another aspect, the invention features a method of producing a recombinant therapeutic antibody preparation (e.g., abciximab, adalimumab, alemtuzumab, basiliximab, bevacizumab, certolizumab, cetuximab, daclizumab, eculizumab, efalizumab, gemtuzumab, ibritumomab, infliximab, muromonab-CD3, natalizumab, omalizumab, palivizumab, panitumumab, ranibizumab, rituximab, tositumomab, or trastuzumab), the method comprising: (a) providing a target value (e.g., a predetermined pharmaceutical product specification or a quality control criterion for a pharmaceutical preparation, e.g., a Certificate of Analysis (CofA), a Certificate of Testing (CofT), or a Master Batch Record of a reference therapeutic antibody product) of one or more of high mannose glycans (e.g., HM3, HM4, HM5, HM6, HM7, HM8, HM9, or combinations thereof) and fucosylated glycans; (b) providing a CHO cell genetically engineered to express a recombinant antibody; (c) culturing the cell in a culture medium comprising 0.1% to 5% DMSO (e.g., at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%. 4.5%, 4.6%, 4.7%, 4.8%, 4.9%, 5% DMSO, or about 0.1% to 5% DMSO, about 0.1% to about 1% DMSO, about 1% to about 2% DMSO, about 2% to about 3% DMSO, about 3% to about 4% DMSO, about 4% to about 5% DMSO, about 0.1% to about 2.5% DMSO, about 2.5% to about 5% DMSO, about 0.1% to about 2% DMSO, about 0.1% to about 3% DMSO, about 0.1% to about 4% DMSO, about 1% to about 5% DMSO, about 2% to about 5% DMSO, or about 3% to about 5% DMSO) under conditions in which the cell expresses the recombinant antibody; (d) harvesting (e.g., purifying or isolating from the cell and/or culture medium) a preparation of the recombinant antibody produced by the cell; and (e) formulating (e.g., one or more of formulating, filling into a container, labeling, packaging) the preparation into a drug product if the preparation meets the target value of the one or more of high mannose glycans and fucosylated glycans.

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

DETAILED DESCRIPTION

Figure 1:
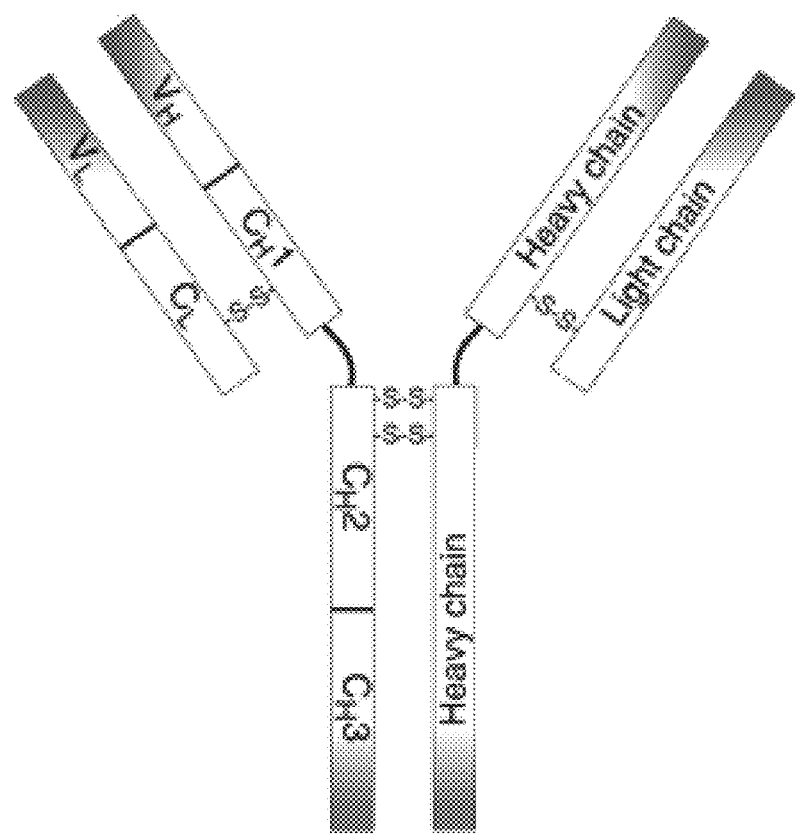
FIG. 1 is a schematic illustration of an IgG antibody molecule.

The inventors have discovered that preparations of polypeptides (e.g., antibodies) having targeted levels of glycans (e.g., high mannose glycans, fucosylated glycans, and/or sialylated glycans) can be produced from cells cultured in a medium having dimethylsulfoxide (DMSO), e.g., a particular level of DMSO effective to cause such effect. Surprisingly, culturing the cells in medium comprising DMSO does not affect cell growth, cell viability, or titer. The present disclosure encompasses preparations of polypeptides (e.g., antibodies) having targeted levels of glycans (e.g., high mannose glycans, fucosylated glycans, and/or sialylated glycans), methods of making such polypeptides (e.g., antibodies), and methods of using such polypeptides (e.g., antibodies).

Definitions

As used herein, "purified" (or "isolated") refers to a nucleic acid sequence (e.g., a polynucleotide) or an amino acid sequence (e.g., a polypeptide) that is substantially free of other components. In some embodiments, a purified polynucleotide or purified polypeptide is removed or separated from other components present in its natural environment. For example, an isolated polypeptide is one that is separated from other components of a cell in which it was produced (e.g., the endoplasmic reticulum or cytoplasmic proteins and RNA). An isolated polynucleotide is one that is separated from other nuclear components (e.g., histones) and/or from upstream or downstream nucleic acid sequences. An isolated nucleic acid sequence or amino acid sequence can be at least 60% free, or at least 75% free, or at least 90% free, or at least 95% free from other components present in natural environment of the indicated nucleic acid sequence or amino acid sequence.

As used herein, "polynucleotide" (or "nucleotide sequence" or "nucleic acid molecule") refers to an oligonucleotide, nucleotide, or polynucleotide, and fragments or portions thereof, and to DNA and RNA of genomic or synthetic origin, which may be single- or double-stranded, and represent the sense or anti-sense strand.

As used herein, "polypeptide" (or "amino acid sequence" or "protein") refers to an oligopeptide, peptide, polypeptide, or protein sequence, and fragments or portions thereof, and to naturally occurring or synthetic molecules. "Amino acid sequence" and like terms, such as "polypeptide" or "protein", are not meant to limit the indicated amino acid sequence to the complete, native amino acid sequence associated with the recited protein molecule.

The term "pharmaceutically effective amount" or "therapeutically effective amount" refers to an amount (e.g., dose) effective in treating a patient, having a disorder or condition described herein. It is also to be understood herein that a "pharmaceutically effective amount" may be interpreted as an amount giving a desired therapeutic effect, either taken in one dose or in any dosage or route, taken alone or in combination with other therapeutic agents.

The term "treatment" or "treating", as used herein, refers to administering a therapy in an amount, manner, and/or mode effective to improve a condition, symptom, or parameter associated with a disorder or condition or to prevent or reduce progression of a disorder or condition, to a degree detectable to one skilled in the art. An effective amount, manner, or mode can vary depending on the subject and may be tailored to the subject.

As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')$_2$, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda. In some embodiments, an antibody includes an Fc region. In some embodiments, an antibody is a therapeutic antibody.

As used herein, the term "Fc region" refers to a dimer of two "Fc polypeptides", each "Fc polypeptide" comprising the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, Va.). For IgA, Fc polypeptide comprises immunoglobulin domains Calpha2 (Cα2) and Calpha3 (Cα3) and the lower part of the hinge between Calpha1 (Cα1) and Cα2. An Fc region can be synthetic, recombinant, or generated from natural sources such as IVIG.

As used herein, a "glycan" is a sugar. Glycans can be monomers or polymers of sugar residues, but typically contain at least three sugars, and can be linear or branched.

A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'-sulfo N-acetylglucosamine, etc). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

As used herein, a "high mannose glycan" refers to a glycan that includes at least 3 mannose sugar residues and that terminates in a mannose on a non-reducing end of the glycan. In some embodiments, a "high mannose glycan" includes at least 4, 5, 6, 7, 8, 9, 10, 11, or 12 mannose sugar residues.

As used herein, a "sialylated glycan" refers to a glycan that includes at least 1 sialic acid. In some embodiments, a sialylated glycan includes at least 1, 2, 3, or 4 sialic acids. In some embodiments, a sialylated glycan is a monosialylated glycan (e.g., a branched glycan monosialylated on an α1-3 arm of the branched glycan (e.g., with a NeuAc-α2, 6-Gal terminal linkage)), and/or a disialylated glycan (e.g., a branched glycan sialylated on both an α1-3 arm and an α1-6 arm of the branched glycan).

As used herein, the term "glycoprotein preparation" refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one of the glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

The term "glycoform" is used herein to refer to a particular form of a glycoprotein. That is, when a glycoprotein includes a particular polypeptide that has the potential to be linked to different glycans or sets of glycans, then each different version of the glycoprotein (i.e., where the polypeptide is linked to a particular glycan or set of glycans) is referred to as a "glycoform".

"Reference glycoprotein", as used herein, refers to a glycoprotein having substantially the same amino acid sequence as (e.g., having about 95-100% identical amino acids of) a glycoprotein described herein, e.g., a glycoprotein to which it is compared. In some embodiments, a reference glycoprotein is a therapeutic glycoprotein described herein, e.g., an FDA approved therapeutic glycoprotein.

As used herein, an "N-glycosylation site of an Fc region" refers to an amino acid residue within an Fc region to which a glycan is N-linked.

"Target value", as used herein, refers to a predetermined level of one or more particular glycans, such as high mannose glycans, fucosylated glycans, and/or sialylated glycans. In some embodiments, a target value is an absolute value. In some embodiments, a target value is a relative value. In some embodiments, a target value is a level of one or more particular glycans, such as high mannose glycans (e.g., HM3, HM4, HM5, HM6, HM7, HM8, HM9, or combinations), fucosylated glycans (e.g., G0F, G1F, G2F, or combinations), and/or sialylated glycans (e.g., monosialylated, disialylated, or combinations), in a reference glycoprotein product or described in a specification or master batch record for a pharmaceutical product.

In some embodiments, a target value refers to an absolute level of (e.g., number of moles of) one or more glycans (e.g., high mannose glycans (e.g., one or more species of high mannose glycans), fucosylated glycans (e.g., one or more species of fucosylated glycans), and/or sialylated glycans (e.g., one or more species of sialylated glycans) in a glycoprotein preparation. In some embodiments, a target value refers to a level of one or more glycans (e.g., high mannose glycans (e.g., one or more species of high mannose glycans), fucosylated glycans (e.g., one or more species of fucosylated glycans), and/or sialylated glycans (e.g., one or more species of sialylated glycans) in a glycoprotein preparation relative to total level of glycans in the glycoprotein preparation. In some embodiments, a target value is expressed as a "percent", which refers to the number of moles of one or more glycans (e.g., Fc glycans) relative to total moles of glycans (e.g., Fc glycans) in a glycoprotein preparation. In some embodiments, "percent" refers to the number of moles of one or more PNGase F-released Fc glycans relative to total moles of PNGase F-released Fc glycans detected.

Cells

Any host cell that can be used to express a polypeptide of interest (e.g., an antibody) can be used in the methods described herein. The cells can be genetically engineered to contain a recombinant nucleic acid sequence, e.g., a gene, that encodes a polypeptide of interest (e.g., an antibody). For example, useful cells can express a recombinant polypeptide. Recombinant expression of a gene encoding a polypeptide can include construction of an expression vector containing a polynucleotide that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then be cultured by conventional techniques, modified in accordance with the present disclosure, to produce a recombinant polypeptide. A variety of host expression vector systems can be used (see, e.g., U.S. Pat. No. 5,807,715). Such host-expression systems (e.g., genetically engineered host expression systems) can be used to produce polypeptides (e.g., antibodies) and, where desired, subsequently purified. Such host expression systems include, but are not limited to, yeast (e.g., *Saccharomyces* and *Pichia*) transformed with recombinant yeast expression vectors containing polypeptide coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing polypeptide coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For expression in mammalian host cells, viral-based expression systems can be utilized (see, e.g., Logan et al., 1984, *Proc. Natl. Acad. Sci. USA* 8:355-359). The efficiency of expression can be enhanced by the inclusion of appropriate transcription enhancer elements, transcription terminators, etc. (see, e.g., Bittner et al., 1987, *Methods in Enzymol.* 153:516-544).

In addition, a host cell strain can be chosen that modulates the expression of the inserted sequences, or modifies and processes the gene product in the specific fashion desired. Different host cells have characteristic and specific mechanisms for the post-translational processing and modification of proteins and gene products. Appropriate cell lines or host systems can be chosen to ensure the correct modification and processing of the polypeptide (e.g., antibody) expressed. Such cells include, for example, established mammalian cell lines and insect cell lines, animal cells, fungal cells, and yeast cells. Mammalian host cells include, but are not limited to, CHO, Vero, BHK, HeLa, COS, MDCK, HEK-293, NIH-3T3, W138, BT483, Hs578T, HTB2, BT20, T47D, NS0 (a murine myeloma cell line that does not endogenously produce any immunoglobulin chains), CRL7O3O, HsS78Bst cells, PER.C6, SP2/0-Ag14, and hybridoma cells. Additional, nonlimiting examples of animal or mammalian host cells include Chinese hamster ovary cells (CHO), such as CHO-K1 (ATCC CCL-61), DG44 (Chasin et al., 1986, *Som. Cell Molec. Genet.*, 12:555-556; and Kolkekar et al., 1997, *Biochem.*, 36:10901-10909), CHO-DXB11 (G. Urlaub and L. A. Chasin, 1980 *Proc. Natl. Acad. Sci.*, 77: 4216-4220. L. H. Graf, and L. A. Chasin 1982, Molec. Cell. Biol., 2: 93-96), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), CHOK1sv (Edmonds et al., Mol. Biotech. 34:179-190 (2006)), CHO-S(Pichler et al., Biotechnol. Bioeng. 108:386-94 (2011)), dihydrofolate reductase negative CHO cells (CHO/-DHFR, Urlaub and Chasin, 1980, *Proc. Natl. Acad. Sci. USA*, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293 cells subcloned for growth in suspension culture, Graham et al., 1977, *J. Gen. Virol.*, 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, *Biol. Reprod.*, 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TR1 cells (Mather, 1982, *Ann. NY Acad. Sci.*, 383:44-68); MCR 5 cells; and FS4 cells.

For long-term, high-yield production of recombinant proteins, host cells can be engineered to stably express a polypeptide (e.g., antibody). Host cells can be transformed with DNA controlled by appropriate expression control elements known in the art, including promoter, enhancer, sequences, transcription terminators, polyadenylation sites, and selectable markers. Methods commonly known in the art of recombinant DNA technology can be used to select a desired recombinant clone. In some embodiments, a cell is genetically engineered to increase level of expression of an endogenous polypeptide, e.g., by increasing transcription of a gene encoding the polypeptide and/or increasing mRNA stability. In some embodiments, transcription of a gene encoding a polypeptide is increased by: altering the regulatory sequence of the endogenous gene, e.g., in a somatic cell, e.g., by the addition of a positive regulatory element, such as an enhancer or a DNA-binding site for a transcriptional activator; the deletion of a negative regulatory element, such as a DNA-binding site for a transcriptional repressor; and/or replacement of the endogenous regulatory sequence, or elements therein, with that of another gene, thereby allowing the coding region of the gene to be transcribed more efficiently.

Once a polypeptide described herein (e.g., an antibody described herein) has been produced by recombinant expression, it can be purified by any method known in the art for purification, for example, by chromatography (e.g., ion exchange, affinity, and sizing column chromatography), centrifugation, differential solubility, or by any other standard technique for the purification of proteins. For example, an antibody can be isolated and purified by appropriately selecting and combining affinity columns such as Protein A column with chromatography columns, filtration, ultra filtration, salting-out and dialysis procedures (see *Antibodies: A Laboratory Manual*, Ed Harlow, David Lane, Cold Spring Harbor Laboratory, 1988). Further, as described herein, a polypeptide (e.g., an antibody) can be fused to heterologous polypeptide sequences to facilitate purification. Polypeptides having desired sugar chains can be separated with a lectin column by methods known in the art (see, e.g., WO 02/30954).

In accordance with the present disclosure, there may be employed conventional molecular biology, microbiology, and recombinant DNA techniques within the skill of the art. Such techniques are described in the literature (see, e.g., Sambrook, Fritsch & Maniatis, *Molecular Cloning: A Laboratory Manual*, Second Edition (1989) Cold Spring Harbor Laboratory Press, Cold Spring Harbor, N.Y.; *DNA Cloning: A Practical Approach*, Volumes I and II (D. N. Glover ed. 1985); Oligonucleotide Synthesis (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells and Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

Culture Methods

In general, polypeptides (e.g., antibodies) having target levels of glycans (e.g., high mannose glycans, fucosylated glycans and/or sialylated glycans) can be produced by culturing cells in media that contains DMSO, e.g., a particular, effective level of DMSO (e.g., during one or more stages of culture).

In some embodiments, cells genetically engineered to express a polypeptide are cultured (e.g., at one or more stages of culture) in a medium that includes DMSO, e.g., an elevated level of DMSO, to decrease levels of G0F glycans and/or fucosylated glycans in a preparation of the polypeptide expressed by the cells. In some embodiments, a level of G0F glycans and/or fucosylated glycans is decreased relative to the corresponding level(s) in a preparation of the polypeptide produced using the same medium that does not include DMSO, e.g., an elevated level of DMSO. In some embodiments, the decreased level of G0F glycans and/or fucosylated glycans is lower than the corresponding level(s) by at least about 10%, 20%, 30%, 40%, 50%, 60%, 70%, 80%, 90%, 95%, or 100%, of the corresponding level.

In some embodiments, cells genetically engineered to express a polypeptide are cultured (e.g., at one or more stages of culture) in a medium that includes DMSO, e.g., an elevated level of DMSO, to increase levels of high mannose glycans, afucosylated glycans, and/or sialylated glycans in a preparation of the polypeptide expressed by the cells. In some embodiments, a level of high mannose glycans, afucosylated glycans, and/or sialylated glycans is increased relative to the corresponding level(s) in a preparation of the polypeptide produced using the same medium that does not include DMSO, e.g., an elevated level of DMSO. In some embodiments, the increased level of high mannose glycans, afucosylated glycans, and/or sialylated glycans is higher than the corresponding level(s) by at least about 10%, 20%, 30%, 40%, 50%, 60%, 70%, 80%, 90%, 100%, 150%, 200%, 250%, 300%, 350%, 400%, 450%, 500%, or more, of the corresponding level.

In some embodiments, cells genetically engineered to express a polypeptide are cultured (e.g., at one or more stages of culture) in a medium that includes a reduced level of DMSO, e.g., does not include DMSO, to increase levels of G0F glycans and/or fucosylated glycans in a preparation of the polypeptide expressed by the cells. In some embodiments, a level of G0F glycans and/or fucosylated glycans is increased relative to the corresponding level(s) in a preparation of the polypeptide produced using the same medium that does not include a reduced level of DMSO. In some embodiments, the increased level of G0F glycans and/or fucosylated glycans is higher than the corresponding level(s) by at least about 10%, 20%, 30%, 40%, 50%, 60%, 70%, 80%, 90%, 100%, 150%, 200%, 250%, 300%, 350%, 400%, 450%, 500%, or more, of the corresponding level.

In some embodiments, cells genetically engineered to express a polypeptide are cultured (e.g., at one or more stages of culture) in a medium that includes a reduced level of DMSO, e.g., does not include DMSO, to decrease levels of high mannose glycans, afucosylated glycans, and/or sialylated glycans in a preparation of the polypeptide expressed by the cells. In some embodiments, a level of high mannose glycans, afucosylated glycans, and/or sialylated glycans is decreased relative to the corresponding level(s) in a preparation of the polypeptide produced using the same medium that does not include a reduced level of DMSO. In some embodiments, the decreased level of high mannose glycans, afucosylated glycans, and/or sialylated glycans is lower than the corresponding level(s) by at least about 10%, 20%, 30%, 40%, 50%, 60%, 70%, 80%, 90%, 95%, or 100%, of the corresponding level.

As used herein, an "elevated level of DMSO" means a higher concentration of DMSO than is present in a standard medium, a starting medium, a medium used at one or more stages of culture, and/or in a medium in which a polypeptide is produced. In some embodiments, DMSO is not present in a standard and/or starting medium, a medium used at one or more other stages of culture, and/or in a medium in which a polypeptide is produced, and an "elevated level" is any amount of DMSO. A medium can include an elevated level of DMSO initially (i.e., at the start of a culture), and/or medium can be supplemented with DMSO to achieve an elevated level of DMSO at a particular time or times (e.g., at one or more stages) during culturing.

In some embodiments, an elevated level of DMSO is an increase of at least about 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000% or more, relative to a level of DMSO in a standard medium, a starting medium, a medium during one or more stages of culture, and/or in a medium in which a polypeptide is produced.

In some embodiments, an elevated level of DMSO is an increase in level (v/v) of DMSO of at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, or more (v/v) DMSO, relative to a level (v/v) of DMSO in a standard medium, a starting medium, a medium during one or more stages of culture, and/or in a medium in which a polypeptide is produced.

In some embodiments, an elevated level of DMSO is about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, or higher (v/v) DMSO. In some embodiments, an elevated level of DMSO is about 0.1% to about 5% DMSO, e.g., about 0.1% to about 1% DMSO, about 1% to about 2% DMSO, about 2% to about 3% DMSO, about 3% to about 4% DMSO, about 4% to about 5% DMSO, about 0.1% to about 2.5% DMSO, about 2.5% to about 5% DMSO, about 0.1% to about 2% DMSO, about 0.1% to about 3% DMSO, about 0.1% to about 4% DMSO, about 1% to about 5% DMSO, about 2% to about 5% DMSO, or about 3% to about 5% DMSO.

As used herein, a "reduced level of DMSO" means a lower concentration of DMSO than is present in a standard medium, a starting medium, a medium used at one or more stages of culture, and/or in a medium in which a polypeptide is produced. A medium can include a reduced level of DMSO initially (i.e., at the start of a culture), a medium can be diluted at a particular time or times (e.g., at one or more stages) during culturing to reduce the level of DMSO, and/or a medium can be replaced with a medium having a reduced level of DMSO at a particular time or times (e.g., at one or more stages) during culturing. In some embodiments, a reduced level of DMSO is 0% (v/v) DMSO or no detectable level of DMSO in a medium.

In some embodiments, a reduced level of DMSO is a decrease of at least about 10%, 20%, 30%, 40%, 50%, 60%, 70%, 80%, 90%, or 100%, relative to a level of DMSO in a standard medium, a starting medium, a medium during one or more stages of culture, and/or in a medium in which a polypeptide is produced.

In some embodiments, a reduced level of DMSO is a decrease in level (v/v) of DMSO of at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, or more, (v/v) DMSO, relative to a level (v/v) of DMSO in a standard medium, a starting medium, a medium during one or more stages of culture, and/or in a medium in which a polypeptide is produced.

In some embodiments, a reduced level of DMSO is less than about 5%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1%; or is 0% (v/v) DMSO.

Cells can be cultured in a variety of cell culture media known in the art, which are modified according to the disclosure to include DMSO as described herein. Cell culture medium is understood by those of skill in the art to refer to a nutrient solution in which cells, such as animal or mammalian cells, are grown. A cell culture medium generally includes one or more of the following components: an energy source (e.g., a carbohydrate such as glucose); amino acids; vitamins; lipids or free fatty acids; and trace elements, e.g., inorganic compounds or naturally occurring elements in the micromolar range. Cell culture medium can also contain additional components, such as hormones and other growth factors (e.g., insulin, transferrin, epidermal growth factor, serum, and the like); salts (e.g., calcium, magnesium and phosphate); buffers (e.g., HEPES); nucleosides and bases (e.g., adenosine, thymidine, hypoxanthine); antibiotics (e.g., gentamycin); and cell protective agents (e.g., a Pluronic polyol (Pluronic F68)).

In some embodiments, in addition to an elevated or reduced level of DMSO, a cell culture medium includes lysine, cysteine, ammonium, manganese, copper, cobalt, putrescine, a peptone, glucose, galactose, galactosamine, glucosamine, glutamine, a lipid (e.g., cholesterol), and/or dextran sulfate. For example, a culture medium can include about 0.1 g/L to about 30 g/L lysine; about 0.1 g/L to about 1 g/L cysteine; about 1 mM to about 50 mM ammonium; about 0.01 mM to about 0.5 mM manganese; about 0.1 µM to about 0.5 mM copper; about 0.1 mg/L to about 30 mg/L cobalt; about 0.01 mg/L to about 5 mg/L putrescine; about 0.1 g/L to about 10 g/L glucose; about 0.5 g/L to about 30 g/L peptone, e.g., a non-animal derived peptone such as soy or cottonseed; about 1 µM to about 1 mM galactosamine; about 0.1 g/L to about 5 g/L glucosamine; and/or about 0.01 g/L to about 0.1 g/L dextran sulfate.

Media that has been prepared or commercially available can be modified according to the present disclosure for utilization in the methods described herein. Nonlimiting examples of such media include Minimal Essential Medium (MEM, Sigma, St. Louis, Mo.); Ham's F10 Medium (Sigma); Dulbecco's Modified Eagles Medium (DMEM, Sigma); RPM 1-1640 Medium (Sigma); HyClone cell culture medium (HyClone, Logan, Utah); Power CHO2 (Lonza Inc., Allendale, N.J.); and chemically-defined (CD) media, which are formulated for particular cell types, e.g., CD-CHO Medium (Invitrogen, Carlsbad, Calif.). Culture medium suitable for particular cells being cultured can be determined by a person of ordinary skill in the art without undue experimentation, and such medium can be altered according to the disclosure.

Cell culture conditions (including pH, $O_2$, $CO_2$, agitation rate and temperature) suitable for cellular production of polypeptides described herein (e.g., antibodies) are those that are known in the art, such as conditions for batch, continuous, or fed-batch culturing of cells. For example, pH of cell culture medium is generally maintained at about 6.8 to about 7.2.

In some embodiments, cells are cultured in one or more stages, and cells can be cultured in medium having an elevated or reduced level of DMSO in one or more stages. For example, a culture method can include a first stage (e.g., using a medium having a reduced level of DMSO) and a second stage (e.g., using a medium having an elevated level of DMSO). In some embodiments, a culture method can include a first stage (e.g., using a medium having an elevated level of DMSO) and a second stage (e.g., using a medium having a reduced level of DMSO). In some embodiments, a culture method includes more than two stages, e.g., 3, 4, 5, 6, or more stages, and any stage can include medium having an elevated level of DMSO or a reduced level of DMSO. The length of culture is not limiting. For example, a culture method can be 5, 6, 7, 8, 9, 10, 11, 12, 13, 14, 15, 16, 17, 18, 19, 20, or more days. In some embodiments, a culture method includes at least two stages. For example, a first stage can include culturing cells in medium having a reduced level of DMSO (e.g., for about 1, 2, 3, 4, 5, 6, 7, 8, 9, 10, or more days), and a second stage can include culturing cells in medium having an elevated level of DMSO (e.g., for about 1, 2, 3, 4, 5, 6, 7, 8, 9, 10, or more days).

In some embodiments, cells are cultured in an initial medium having a reduced level of DMSO for 5 days, and medium having an elevated of DMSO is added to the culture of cells on day 6.

In some embodiments, a first stage of culture is a growth stage. Generally, during a growth stage, a cell culture undergoes a period of exponential cell growth (the log phase) where cells are generally rapidly dividing. In some embodiments, cells are cultured under such conditions such that cell growth is maximized. The growth cycle and conditions for maximizing growth of host cells can be determined for a particular host cell by a person of ordinary skill in the art without undue experimentation. In some embodiments, cells are maintained in a growth stage for a period of between 1 and 10 days. In some embodiments, cells are cultured in a medium having a reduced level of DMSO or an elevated level of DMSO for all or part of a growth stage.

In some embodiments, a second stage of culture is a production stage. Generally, during a production stage, cell growth has plateaued or is maintained at a near constant level. During a production stage, logarithmic cell growth has ended and polypeptide production is increased. During this period of time, a medium can generally be supplemented to support continued polypeptide production and to achieve a desired polypeptide product. In some embodiments, cells are maintained in a production stage for a period of between 1 and 10 days. In some embodiments, cells are cultured in a medium having a reduced level of DMSO or an elevated level of DMSO for all or part of a production stage.

In general, cell culture methods are classified as batch culture, continuous culture, and fed-batch culture. Any of these culture methods can be used to grow cells that produce polypeptides (e.g., antibodies) having targeted levels of glycans (e.g., high mannose glycans, fucosylated glycans, and/or sialylated glycans).

Batch Culture

In batch culture, a small amount of seed culture solution is added to a medium and cells are grown without any addition of a new medium or discharge of culture solution during culture. For the production of polypeptides (e.g., antibodies) having targeted levels of glycans (e.g., high mannose glycans, fucosylated glycans, and/or sialylated glycans) using batch culture, the medium comprises an elevated level or a reduced level of DMSO at an initial stage of cell culture.

In some embodiments, polypeptides (e.g., antibodies) having targeted levels of glycans (e.g., high mannose glycans, fucosylated glycans, and/or sialylated glycans) are produced by batch culture of cells expressing the polypeptide in a medium having an elevated level of DMSO. In some embodiments, cells are cultured in a medium having at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, or higher (v/v) DMSO. In some embodiments, cells are cultured in a medium having at least about 0.1% to about 5% DMSO, e.g., about 0.1% to about 1% DMSO, about 1% to about 2% DMSO, about 2% to about 3% DMSO, about 3% to about 4% DMSO, about 4% to about 5% DMSO, about 0.1% to about 2.5% DMSO, about 2.5% to about 5% DMSO, about 0.1% to about 2% DMSO, about 0.1% to about 3% DMSO, about 0.1% to about 4% DMSO, about 1% to about 5% DMSO, about 2% to about 5% DMSO, or about 3% to about 5% DMSO.

In some embodiments, polypeptides (e.g., antibodies) having targeted levels of glycans (e.g., high mannose glycans, fucosylated glycans, and/or sialylated glycans) are produced by batch culture of cells expressing the polypeptide in a medium having a reduced level of DMSO. In some embodiments, cells are cultured in a medium having less than about 5%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1%; or having 0% (v/v) DMSO.

Continuous Culture

Continuous culture is a culture method in which a medium is added and discharged continuously during culture. This continuous method includes perfusion culture. For example, in the production of polypeptides (e.g., antibodies) having targeted levels of glycans (e.g., high mannose glycans, fucosylated glycans, and/or sialylated glycans) using continuous culture, level of DMSO in the medium can be adjusted at one or more stages of culture to result in an elevated level or a reduced level of DMSO. In certain methods, culture medium used at a first stage of culture does not include an elevated level or a reduced level of DMSO, but at a particular time point during continuous culture (such as during all or part of a growth stage and/or a production stage), medium added during culture is elevated or reduced in the level of DMSO.

In some embodiments, polypeptides (e.g., antibodies) having targeted levels of glycans (e.g., high mannose glycans, fucosylated glycans, and/or sialylated glycans) are produced by continuous culture of cells expressing the polypeptide in a medium having an elevated level of DMSO (e.g., during one or more stages of continuous culture). In some embodiments, cells are cultured, during one or more stages of continuous culture, in a medium having at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, or higher (v/v) DMSO. In some embodiments, cells are cultured, during one or more stages of continuous culture, in a medium having at least about 0.1% to about 5% DMSO, e.g., about 0.1% to about 1% DMSO, about 1% to about 2% DMSO, about 2% to about 3% DMSO, about 3% to about 4% DMSO, about 4% to about 5% DMSO, about 0.1% to about 2.5% DMSO, about 2.5% to about 5% DMSO, about 0.1% to about 2% DMSO, about 0.1% to about 3% DMSO, about 0.1% to about 4% DMSO, about 1% to about 5% DMSO, about 2% to about 5% DMSO, or about 3% to about 5% DMSO.

In some embodiments, cells are cultured, during one or more stages of continuous culture, in a medium having a reduced level of DMSO. In some embodiments, cells are cultured, during one or more stages of continuous culture, in a medium having less than about 5%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1%; or having 0% (v/v) DMSO.

Fed-Batch Culture

Fed-batch culture is a method between batch culture and continuous culture. In a fed-batch culture, a cell culture is fed or supplemented continuously or sequentially during culture, but unlike continuous culture, discharge of culture solution is not carried out during culture. For example, for the production of polypeptides (e.g., antibodies) having targeted levels of glycans (e.g., high mannose glycans, fucosylated glycans, and/or sialylated glycans) using fed-batch culture, medium added during one or more stages of culture can have an elevated level or a reduced level of DMSO.

In some embodiments, polypeptides (e.g., antibodies) having targeted levels of glycans (e.g., high mannose glycans, fucosylated glycans, and/or sialylated glycans) are produced by adding medium (at one or more stages) to a fed batch culture of cells expressing the polypeptide sufficient to achieve (at one or more stages) an elevated level of DMSO. In some embodiments, at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, or higher (v/v) DMSO in the culture medium is achieved (e.g., by adding or supplementing with DMSO, e.g., at one or more stages). In some embodiments, a level of DMSO of at least about 0.1% to about 5% DMSO, e.g., about 0.1% to about 1% DMSO, about 1% to about 2% DMSO, about 2% to about 3% DMSO, about 3% to about 4% DMSO, about 4% to about 5% DMSO, about 0.1% to about 2.5% DMSO, about 2.5% to about 5% DMSO, about 0.1% to about 2% DMSO, about 0.1% to about 3% DMSO, about 0.1% to about 4% DMSO, about 1% to about 5% DMSO, about 2% to about 5% DMSO, or about 3% to about 5% DMSO, is achieved.

In some embodiments, polypeptides (e.g., antibodies) having targeted levels of glycans (e.g., high mannose glycans, fucosylated glycans, and/or sialylated glycans) are produced by adding medium (at one or more stages) to a fed batch culture of cells expressing the polypeptide sufficient to achieve (at one or more stages) a reduced level of DMSO. In some embodiments, less than about 5%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1%; or 0% (v/v) DMSO in the culture medium is achieved (at one or more stages).

According to the present disclosure, cell culture can be carried out under conditions for large or small scale production of polypeptides (e.g., antibodies), using culture vessels and/or culture apparatuses that are conventionally employed for animal or mammalian cell culture. For example, tissue culture dishes, T-flasks, shaker flasks, and spinner flasks can be used on a laboratory scale. For culturing on a larger scale (e.g., 1 L, 10 L, 100 L, 500 L, 5000 L, or more), a fluidized bed bioreactor, a hollow fiber bioreactor, a roller bottle culture, or a stirred tank bioreactor system can be used (e.g., as described in U.S. Pat. Nos. 7,541,164 and 7,332,303).

In particular methods, levels of one or more glycans (e.g., high mannose glycans, fucosylated glycans, and/or sialylated glycans) in a preparation of polypeptides (e.g., antibodies) are monitored during one or more times (e.g., one or more stages) of cell culture, thereby allowing adjustment (e.g., increasing or decreasing the amount of DMSO in the culture) or possibly termination of the culture in order, for example, to achieve a target level of polypeptides (e.g., antibodies) having targeted levels of glycans (e.g., high mannose glycans, fucosylated glycans, and/or sialylated glycans).

Polypeptides

Described herein are therapeutic preparations of polypeptides (e.g., glycoproteins), and methods of making and using such preparations. Glycoproteins include, for example, any of a variety of hematologic agents (including, for instance, erythropoietin, blood-clotting factors, etc.), interferons, colony stimulating factors, antibodies, enzymes, and hormones. The identity of a particular glycoprotein is not intended to limit the present disclosure, and a therapeutic preparation described herein can include any glycoprotein of interest, e.g., a glycoprotein having an Fc region.

A glycoprotein described herein can include a target-binding domain that binds to a target of interest (e.g., binds to an antigen). For example, a glycoprotein, such as an antibody, can bind to a transmembrane polypeptide (e.g., receptor) or ligand (e.g., a growth factor). Exemplary molecular targets (e.g., antigens) for glycoproteins described herein (e.g., antibodies) include CD proteins such as CD2, CD3, CD4, CD8, CD11, CD19, CD20, CD22, CD25, CD33, CD34, CD40, CD52; members of the ErbB receptor family such as the EGF receptor (EGFR, HER1, ErbB1), HER2 (ErbB2), HER3 (ErbB3) or HER4 (ErbB4) receptor; macrophage receptors such as CRIg; tumor necrosis factors such as TNFα or TRAIL/Apo-2; cell adhesion molecules such as LFA-1, Mac1, p150,95, VLA-4, ICAM-1, VCAM and αvβ3 integrin including either α or β subunits thereof (e.g., anti-CD11a, anti-CD18 or anti-CD11b antibodies); growth factors and receptors such as EGF, FGFR (e.g., FGFR3) and VEGF; IgE; cytokines such as IL1; cytokine receptors such as IL2 receptor; blood group antigens; flk2/flt3 receptor; obesity (OB) receptor; mpl receptor; CTLA-4; protein C; neutropilins; ephrins and receptors; netrins and receptors; slit and receptors; chemokines and chemokine receptors such as CCL5, CCR4, CCR5; amyloid beta; complement factors, such as complement factor D; lipoproteins, such as oxidized LDL (oxLDL); lymphotoxins, such as lymphotoxin alpha (LTa). Other molecular targets include Tweak, B7RP-1, proprotein convertase subtilisin/kexin type 9 (PCSK9), sclerostin, c-kit, Tie-2, c-fms, and anti-M1.

Reference Polypeptides

In some embodiments, described herein are therapeutic polypeptide (e.g., glycoprotein) having targeted levels of glycans (e.g., high mannose glycans, fucosylated glycans, and/or sialylated glycans), where the targeted levels are the levels of glycans (e.g., high mannose glycans, fucosylated glycans, and/or sialylated glycans) in a reference polypeptide product (e.g., glycoprotein product). Nonlimiting, exemplary reference glycoprotein products can include abatacept (Orencia®, Bristol-Myers Squibb), abciximab (ReoPro®, Roche), adalimumab (Humira®, Bristol-Myers Squibb), aflibercept (Eylea®, Regeneron Pharmaceuticals), alefacept (Amevive®, Astellas Pharma), alemtuzumab (Campath®, Genzyme/Bayer), basiliximab (Simulect®, Novartis), belatacept (Nulojix®, Bristol-Myers Squibb), belimumab (Benlysta®, GlaxoSmithKline), bevacizumab (Avastin®, Roche), canakinumab (Ilaris®, Novartis), brentuximab vedotin (Adcetris®, Seattle Genetics), certolizumab (CIMZIA®, UCB, Brussels, Belgium), cetuximab (Erbitux®, Merck-Serono), daclizumab (Zenapax®, Hoffmann-La Roche), denileukin diftitox (Ontak®, Eisai), denosumab (Prolia®, Amgen; Xgeva®, Amgen), eculizumab (Soliris®, Alexion Pharmaceuticals), efalizumab (Raptiva®, Genentech), etanercept (Enbrel®, Amgen-Pfizer), gemtuzumab (Mylotarg®, Pfizer), golimumab (Simponi®, Janssen), ibritumomab (Zevalin®, Spectrum Pharmaceuticals), infliximab (Remicade®, Centocor), ipilimumab (Yervoy™ Bristol-Myers Squibb), muromonab (Orthoclone OKT3®, Janssen-Cilag), natalizumab (Tysabri®, Biogen Idec, Elan), ofatumumab (Arzerra®, GlaxoSmithKline), omalizumab (Xolair®, Novartis), palivizumab (Synagis®, MedImmune), panitumumab (Vectibix®, Amgen), ranibizumab (Lucentis®, Genentech), rilonacept (Arcalyst®, Regeneron Pharmaceuticals), rituximab (MabTherat, Roche), tocilizumab (Actemra®, Genentech; RoActemra, Hoffman-La Roche) tositumomab (Bexxar®, GlaxoSmithKline), and trastuzumab (Herceptin®, Roche).

In some embodiments, a level of one or more glycans (e.g., high mannose glycans, fucosylated glycans, and/or sialylated glycans) in a reference polypeptide product is determined by analyzing one or more preparations (e.g., one or more lots) of the reference polypeptide. In some embodiments, a level of one or more glycans (e.g., high mannose glycans, fucosylated glycans, and/or sialylated glycans) in a reference polypeptide product is a range of the one or more glycans in two or more preparations of the reference polypeptide (e.g., two or more lots of the reference polypeptide product). In some embodiments, a level of one or more glycans is a range (e.g., spanning a lowest level of the one or more glycans to a highest level of the one or more glycans) in two or more lots of the reference polypeptide product.

N-Linked Glycosylation

N-linked oligosaccharide chains are added to a protein in the lumen of the endoplasmic reticulum (see Molecular Biology of the Cell, Garland Publishing, Inc. (Alberts et al., 1994)). Specifically, an initial oligosaccharide (typically 14-sugar) is added to the amino group on the side chain of an asparagine residue contained within the target consensus sequence of Asn-X-Ser/Thr, where X may be any amino acid except proline. The structure of this initial oligosaccharide is common to most eukaryotes, and contains 3 glucose, 9 mannose, and 2 N-acetylglucosamine residues. This initial oligosaccharide chain can be trimmed by specific glycosidase enzymes in the endoplasmic reticulum, resulting in a short, branched core oligosaccharide composed of two N-acetylglucosamine and three mannose residues.

N-glycans can be subdivided into three distinct groups called "high mannose type", "hybrid type", and "complex type", with a common pentasaccharide core (Man (alpha1, 6)-(Man(alpha1,3))-Man(beta1,4)-GlcpNAc(beta 1,4)-GlcpNAc(beta 1,N)-Asn) occurring in all three groups.

After initial processing in the endoplasmic reticulum, the glycoprotein is transported to the Golgi where further processing may take place. If the glycan is transferred to the Golgi before it is completely trimmed to the core pentasaccharide structure, it results in a "high-mannose glycan".

Additionally or alternatively, one or more monosaccharides units of N-acetylglucosamine may be added to core mannose subunits to form a "complex glycan". Galactose may be added to N-acetylglucosamine subunits, and sialic acid subunits may be added to galactose subunits, resulting in chains that terminate with any of a sialic acid, a galactose or an N-acetylglucosamine residue. Additionally, a fucose residue may be added to an N-acetylglucosamine residue of the core oligosaccharide. Each of these additions is catalyzed by specific glycosyl transferases, known in the art.

Sialic acids are a family of 9-carbon monosaccharides with heterocyclic ring structures. They bear a negative charge via a carboxylic acid group attached to the ring as well as other chemical decorations including N-acetyl and N-glycolyl groups. The two main types of sialyl residues found in glycoproteins produced in mammalian expression systems are N-acetyl-neuraminic acid (NeuAc) and N-glycolylneuraminic acid (NeuGc). These usually occur as terminal structures attached to galactose (Gal) residues at the non-reducing termini of both N- and O-linked glycans. The glycosidic linkage configurations for these sialyl groups can be either α2,3 or α2,6.

"Hybrid glycans" comprise characteristics of both high-mannose and complex glycans. For example, one branch of a hybrid glycan may comprise primarily or exclusively mannose residues, while another branch may comprise N-acetylglucosamine, sialic acid, and/or galactose sugars.

N-Linked Glycosylation in Antibodies

Antibodies are glycosylated at conserved, N-linked glycosylation sites in the Fc regions of immunoglobulin heavy chains. For example, each heavy chain of an IgG antibody has a single N-linked glycosylation site at Asn297 of the CH2 domain (see Jefferis, Nature Reviews 8:226-234 (2009)). IgA antibodies have N-linked glycosylation sites within the CH2 and CH3 domains, IgE antibodies have N-linked glycosylation sites within the CH3 domain, and IgM antibodies have N-linked glycosylation sites within the CH1, CH2, CH3, and CH4 domains (see Arnold et al., J. Biol. Chem. 280:29080-29087 (2005); Mattu et al., J. Biol. Chem. 273:2260-2272 (1998); Nettleton et al., Int. Arch. Allergy Immunol. 107:328-329 (1995)).

Each antibody isotype has a distinct variety of N-linked carbohydrate structures in the constant regions. For example, IgG has a single N-linked biantennary carbohydrate at Asn297 of the CH2 domain in each Fc polypeptide of the Fc region, which also contains the binding sites for C1q and FcγR (see Jefferis et al., Immunol. Rev. 163:59-76 (1998); and Wright et al., Trends Biotech 15:26-32 (1997)). For human IgG, the core oligosaccharide normally consists of GlcNAc$_2$Man$_3$GlcNAc, with differing numbers of outer residues. Variation among individual IgG can occur via attachment of galactose and/or galactose-sialic acid at one or both terminal GlcNAc or via attachment of a third GlcNAc arm (bisecting GlcNAc), and/or attachment of fucose.

Antibodies

The basic structure of an IgG antibody is illustrated in FIG. 1. As shown in FIG. 1, an IgG antibody consists of two identical light polypeptide chains and two identical heavy polypeptide chains linked together by disulphide bonds. The first domain located at the amino terminus of each chain is variable in amino acid sequence, providing antibody binding specificities found in each individual antibody. These are known as variable heavy (VH) and variable light (VL) regions. The other domains of each chain are relatively invariant in amino acid sequence and are known as constant heavy (CH) and constant light (CL) regions. As shown in FIG. 1, for an IgG antibody, the light chain includes one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

Antibodies described herein can include, for example, monoclonal antibodies, polyclonal antibodies (e.g., IVIG), multispecific antibodies, human antibodies, humanized antibodies, camelized antibodies, chimeric antibodies, single-chain Fvs (scFv), disulfide-linked Fvs (sdFv), and anti-idiotypic (anti-Id) antibodies, and antigen-binding fragments of any of the above. Antibodies can be of any type (e.g., IgG, IgE, IgM, IgD, IgA and IgY), class (e.g., IgG1, IgG2, IgG3, IgG4, IgA1 and IgA2) or subclass.

The term "Fc fragment", as used herein, refers to one or more fragments of an Fc region that retains an Fc function and/or activity described herein, such as binding to an Fc receptor. Examples of such fragments include fragments that include an N-linked glycosylation site of an Fc region (e.g., an Asn297 of an IgG heavy chain or homologous sites of other antibody isotypes), such as a CH2 domain. The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')$_2$ fragment, a Fd fragment, a Fv fragment, a scFv fragment, a dAb fragment (Ward et al., (1989) Nature 341:544-546), and an isolated complementarity determining region (CDR). These antibody fragments can be obtained using conventional techniques known to those with skill in the art, and fragments can be screened for utility in the same manner as are intact antibodies.

Reference glycoproteins described herein (e.g., reference antibodies) or fragments thereof can be produced by any method known in the art for synthesizing glycoproteins (e.g., antibodies) (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645). Chimeric antibodies can be produced using methods described in, e.g., Morrison, 1985, Science 229:1202, and humanized antibodies by methods described in, e.g., U.S. Pat. No. 6,180,370.

Additional reference antibodies described herein are bispecific antibodies and multivalent antibodies, as described in, e.g., Segal et al., J. Immunol. Methods 248:1-6 (2001); and Tuft et al., J. Immunol. 147: 60 (1991).

Glycoprotein Conjugates

The disclosure includes glycoproteins (or Fc regions or Fc fragments containing one or more N-glycosylation sites thereof) that are conjugated or fused to one or more heterologous moieties. Heterologous moieties include, but are not limited to, peptides, polypeptides, proteins, fusion proteins, nucleic acid molecules, small molecules, mimetic agents, synthetic drugs, inorganic molecules, and organic molecules. In some instances, a glycoprotein conjugate is a fusion protein that comprises a peptide, polypeptide, protein scaffold, scFv, dsFv, diabody, Tandab, or an antibody mimetic fused to an Fc region, such as a glycosylated Fc region. A fusion protein can include a linker region connecting an Fc region to a heterologous moiety (see, e.g., Hallewell et al. (1989), J. Biol. Chem. 264, 5260-5268; Alfthan et al. (1995), Protein Eng. 8, 725-731; Robinson & Sauer (1996)).

Exemplary, nonlimiting reference glycoprotein conjugate products include abatacept (Orencia®, Bristol-Myers Squibb), aflibercept (Eylea®, Regeneron Pharmaceuticals), alefacept (Amevive®, Astellas Pharma), belatacept (Nulojix®, Bristol-Myers Squibb), denileukin diftitox (Ontak®, Eisai), etanercept (Enbrel®, Amgen-Pfizer), and rilonacept (Arcalyst®, Regeneron Pharmaceuticals).

In some instances, a glycoprotein conjugate includes an Fc region (or an Fc fragment containing one or more N-glycosylations site thereof) conjugated to a heterologous polypeptide of at least 10, at least 20, at least 30, at least 40, at least 50, at least 60, at least 70, at least 80, at least 90 or at least 100 amino acids.

In some instances, a glycoprotein conjugate includes an Fc region (or an Fc fragment containing one or more N-glycosylation sites thereof) conjugated to one or more marker sequences, such as a peptide to facilitate purification. A particular marker amino acid sequence is a hexa-histidine peptide, such as the tag provided in a pQE vector (QIAGEN, Inc., 9259 Eton Avenue, Chatsworth, Calif., 91311). Other peptide tags useful for purification include, but are not limited to, the hemagglutinin "HA" tag, which corresponds to an epitope derived from the influenza hemagglutinin protein (Wilson et al., 1984, Cell 37:767) and the "Flag" tag.

In other instances, a glycoprotein conjugate includes an Fc region (or Fc fragment containing one or more N-glycosylation sites thereof) conjugated to a diagnostic or detectable agent. Such fusion proteins can be useful for monitoring or prognosing development or progression of disease or disorder as part of a clinical testing procedure, such as determining efficacy of a particular therapy. Such diagnosis and detection can be accomplished by coupling a glycoprotein to detectable substances including, but not limited to, various enzymes, such as but not limited to horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as but not limited to iodine ($^{131}$I, $^{125}$I, $^{123}$I), carbon ($^{14}$C) sulfur ($^{35}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{153}$Gd, $^{159}$Gd, $^{149}$Pm, $^{140}$La, $^{169}$Yb, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{51}$Cr, $^{54}$Mn, $^{75}$Se, $^{113}$Sn, and $^{117}$Sn; positron emitting metals using various positron emission tomographies, non-radioactive paramagnetic metal ions, and molecules that are radiolabelled or conjugated to specific radioisotopes.

Techniques for conjugating therapeutic moieties to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987)).

Glycan Evaluation

In some embodiments, glycans of glycoproteins are analyzed by any available suitable method. In some instances, glycan structure and composition as described herein are analyzed, for example, by one or more, enzymatic, chromatographic, mass spectrometry (MS), chromatographic followed by MS, electrophoretic methods, electrophoretic methods followed by MS, nuclear magnetic resonance (NMR) methods, and combinations thereof. Exemplary enzymatic methods include contacting a glycoprotein preparation with one or more enzymes under conditions and for a time sufficient to release one or more glycan(s) (e.g., one or more exposed glycan(s)). In some instances, the one or more enzymes include(s) PNGase F. Exemplary chromatographic methods include, but are not limited to, Strong Anion Exchange chromatography using Pulsed Amperometric Detection (SAX-PAD), liquid chromatography (LC), high performance liquid chromatography (HPLC), ultra performance liquid chromatography (UPLC), thin layer chromatography (TLC), amide column chromatography, and combinations thereof. Exemplary mass spectrometry (MS) include, but are not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof. Exemplary nuclear magnetic resonance (NMR) include, but are not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some instances, techniques described herein may be combined with one or more other technologies for the detection, analysis, and or isolation of glycans or glycoproteins. For example, in certain instances, glycans are analyzed in accordance with the present disclosure using one or more available methods (to give but a few examples, see Anumula, Anal. Biochem., 350(1):1, 2006; Klein et al., Anal. Biochem., 179:162, 1989; and/or Townsend, R. R. Carbohydrate Analysis" High Performance Liquid Chromatography and Capillary Electrophoresis, Ed. Z. El Rassi, pp 181-209, 1995; WO2008/128216; WO2008/128220; WO2008/128218; WO2008/130926; WO2008/128225; WO2008/130924; WO2008/128221; WO2008/128228; WO2008/128227; WO2008/128230; WO2008/128219; WO2008/128222; WO2010/071817; WO2010/071824; WO2010/085251; WO2011/069056; and WO2011/127322, each of which is incorporated herein by reference in its entirety). For example, in some instances, glycans are characterized using one or more of chromatographic methods, electrophoretic methods, nuclear magnetic resonance methods, and combinations thereof. In some embodiments, glycans are analyzed by labeling with a fluorescent dye and measuring levels of fluorescence.

In some instances, methods for evaluating one or more target protein specific parameters, e.g., in a glycoprotein preparation, e.g., one or more of the parameters disclosed herein, can be performed by one or more of the methods listed in Table 1.

TABLE 1

Exemplary methods of evaluating parameters:

| Method(s) | Relevant literature | Parameter |
|---|---|---|
| C18 UPLC Mass Spec.* | Chen and Flynn, Anal. Biochem., 370: 147-161 (2007)<br>Chen and Flynn, J. Am. Soc. Mass Spectrom., 20: 1821-1833 (2009) | Glycan(s) (e.g., N-linked glycan, exposed N-linked glycan, glycan detection, glycan identification, and characterization; site specific glycation; glycoform detection (e.g., parameters 1-7); percent glycosylation; and/or aglycosyl) |
| Bioanalyzer (reducing/non-reducing)* | Forrer et al., Anal. Biochem., 334: 81-88 (2004) | Glycan (e.g., N-linked glycan, exposed N-linked glycan) (including, for example, glycan detection, identification, and characterization; site specific glycation; glycoform detection; percent glycosylation; and/or aglycosyl) |
| LC-MS (reducing/non-reducing/alkylated)*<br>*Methods include removal (e.g., enzymatic, chemical, and physical) of glycans | Dick et al., Biotechnol. Bioeng., 100: 1132-1143 (2008)<br>Goetze et al., Glycobiol., 21: 949-959 (2011)<br>Xie et al., mAbs, 2: 379-394 (2010) | Glycan (e.g., N-linked glycan, exposed N-linked glycan) (including, for example, glycan detection, identification, and characterization; site specific glycation; glycoform detection; percent glycosylation; and/or aglycosyl) |
| Anion-exchange chromatography | Ahn et al., J. Chrom. B, 878: 403-408 (2010) | Sialylated glycan |
| 1,2-diamino-4,5-methylenedioxybenzene (DMB) labeling method | Hokke et al., FEBS Lett., 275: 9-14 (1990) | Sialic acid |

The literature recited above are hereby incorporated by reference in their entirety or, in the alternative, to the extent that they pertain to one or more of the methods for determining a parameter described herein.

Pharmaceutical Compositions and Administration

A glycoprotein described herein can be incorporated (e.g., formulated) into a pharmaceutical composition. Such a pharmaceutical composition is useful as an alternative and/or improved composition for the prevention and/or treatment of one or more diseases relative to a corresponding reference glycoprotein. Pharmaceutical compositions comprising a glycoprotein can be formulated by methods known to those skilled in the art. The pharmaceutical composition can be administered parenterally in the form of an injectable formulation comprising a sterile solution or suspension in water or another pharmaceutically acceptable liquid. For example, the pharmaceutical composition can be formulated by suitably combining the glycoprotein with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided.

A sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

Nonlimiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. A formulated injection can be packaged in a suitable ampule.

In some instances, a level of one or more glycans described herein can be compared to a predetermined level (e.g., a corresponding level in a reference standard), e.g., to make a decision regarding the composition of the polypeptide preparation, e.g., a decision to classify, select, accept or discard, release or withhold, process into a drug product, ship, move to a different location, formulate, label, package, release into commerce, or sell or offer for sale the polypeptide, e.g., a recombinant antibody. In other instances, the decision can be to accept, modify or reject a production parameter or parameters used to make the polypeptide, e.g., an antibody. Particular, nonlimiting examples of reference standards include a control level (e.g., a polypeptide produced by a different method) or a range or value in a product specification (e.g., an FDA label or Physician's Insert) or quality criterion for a pharmaceutical preparation containing the polypeptide preparation.

In some instances, methods (i.e., evaluation, identification, and production methods) include taking action (e.g., physical action) in response to the methods disclosed herein. For example, a polypeptide preparation is classified, selected, accepted or discarded, released or withheld, processed into a drug product, shipped, moved to a different location, formulated, labeled, packaged, released into commerce, or sold or offered for sale, depending on whether the preselected or target value is met. In some instances, processing may include formulating (e.g., combining with pharmaceutical excipients), packaging (e.g., in a syringe or vial), labeling, or shipping at least a portion of the polypeptide preparation. In some instances, processing includes formulating (e.g., combining with pharmaceutical excipients), packaging (e.g., in a syringe or vial), and labeling at least a portion of the preparation as a drug product described herein. Processing can include directing and/or contracting another party to process as described herein.

In some instances, a biological activity of a polypeptide preparation (e.g., an antibody preparation) is assessed. Biological activity of the preparation can be analyzed by any known method. In some embodiments, a binding activity of a polypeptide is assessed (e.g., binding to a receptor). In some embodiments, a therapeutic activity of a polypeptide is assessed (e.g., an activity of a polypeptide in decreasing severity or symptom of a disease or condition, or in delaying appearance of a symptom of a disease or condition). In some embodiments, a pharmacologic activity of a polypeptide is assessed (e.g., bioavailability, pharmacokinetics, pharmacodynamics). For methods of analyzing bioavailability, pharmacokinetics, and pharmacodynamics of glycoprotein therapeutics, see, e.g., Weiner et al., J. Pharm. Biomed. Anal. 15(5):571-9, 1997; Srinivas et al., J. Pharm. Sci. 85(1):1-4, 1996; and Srinivas et al., Pharm. Res. 14(7):911-6, 1997.

The particular biological activity or therapeutic activity that can be tested will vary depending on the particular polypeptide (e.g., antibody). The potential adverse activity or toxicity (e.g., propensity to cause hypertension, allergic reactions, thrombotic events, seizures, or other adverse events) of polypeptide preparations can be analyzed by any available method. In some embodiments, immunogenicity of a polypeptide preparation is assessed, e.g., by determining whether the preparation elicits an antibody response in a subject.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

A suitable means of administration can be selected based on the age and condition of the patient. A single dose of the pharmaceutical composition containing a modified glycoprotein can be selected from a range of 0.001 to 1000 mg/kg of body weight. On the other hand, a dose can be selected in the range of 0.001 to 100000 mg/body weight, but the present disclosure is not limited to such ranges. The dose and method of administration varies depending on the weight, age, condition, and the like of the patient, and can be suitably selected as needed by those skilled in the art.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following example. The example is provided for illustrative purposes only. It is not to be construed as limiting the scope or content of the disclosure in any way.

EXAMPLE

Effect of DMSO on Glycosylation

Methods

The effect of DMSO on antibody glycoforms of a model antibody produced by CHO cells was analyzed. CHO cells were grown initially in base media (Power CHO2, Catalog #BE15-771, Lonza Inc., Allendale, N.J.) containing soy hydrolysate, Lonza Power Feed A and additional supplements. On Day 3, the cells were fed with Lonza Power Feed A and soy hydrolysate. On Day 6, the cells were fed with Lonza Power Feed A medium and additional supplements with 2.5% DMSO (final concentration) or without DMSO. Cells were fed 2 g/L glucose when the glucose concentration dropped below 2 g/L. Cells were harvested on Days 10, 12, or 14, and the antibodies produced were evaluated for titer and glycan composition.

Relative quantitation of each glycoform was performed on glycans enzymatically released from the antibody using PNGase F and labeled with the fluorophore 2-aminobenzamide. The relative quantities were based on the fluorescence intensity of the relevant species relative to the total fluorescence intensity in the chromatogram. All glycoforms eluting at the same retention time were considered together.

Results

The presence or absence of DMSO in the culture medium had minimal impact on titer or maximum VCD. Cells grown in the presence of DMSO had an average maximum VCD of $8.0 \times 10^6$ cells/mL and a titer of 1.02 g/L, whereas cells grown in the absence of DMSO had an average maximum VCD of $8.1 \times 10^6$ cells/mL and a titer of 0.92 g/L.

Figure 2A:
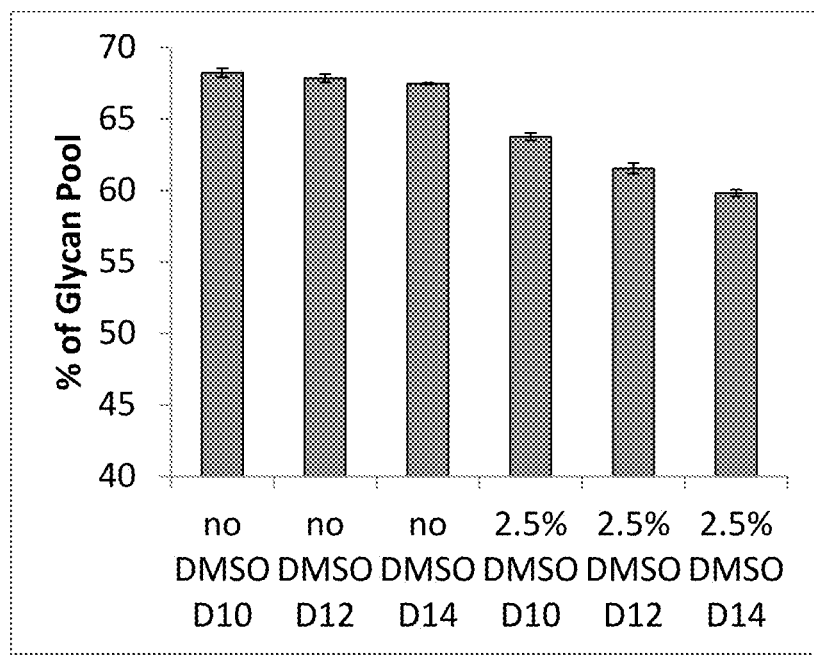
FIG. 2A is a graphic representation of G0F glycan levels in preparations of a model antibody from cells grown in medium with or without DMSO.
Figure 2B:
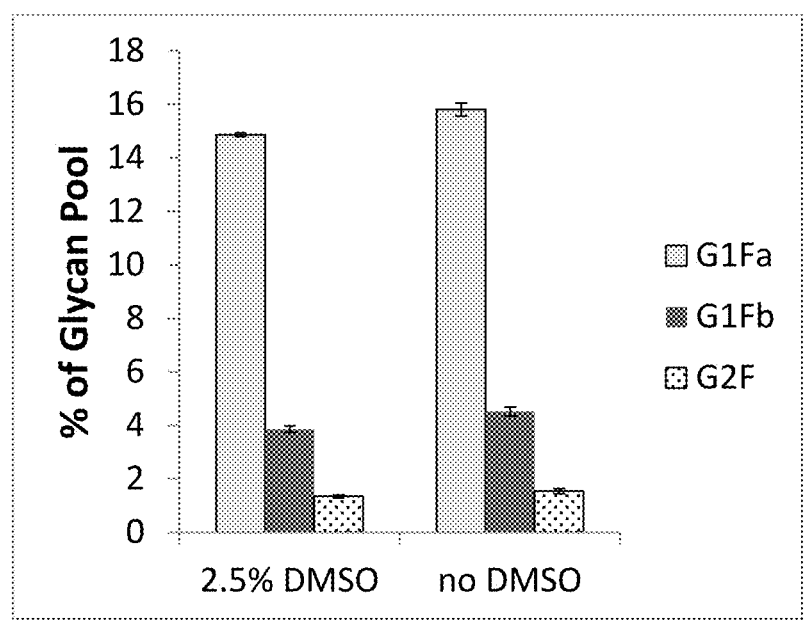
FIG. 2B is a graphic representation of the two G1F isomers (indicated as G1Fa and G1Fb), or G2F glycan levels in preparations of a model antibody from cells grown in medium with or without DMSO.

As shown in FIG. 2A, the level of G0F was decreased in antibodies grown in the presence of DMSO (about 7% decrease on day 14). Surprisingly, as shown in FIG. 2B, the levels of G1F and G2F were only slightly impacted by the presence of DMSO (by about 1% or less). This indicates that the presence of DMSO did not shift the G0F/G1F/G2F distribution by altering galactosylation levels. Rather, this finding suggests that G0F was diverted to other species. A concomitant increase was seen in 3,3,1,0,0 glycans (structure shown in FIG. 6; data not shown). As 3,3,1,0,0 is converted to G0F by GnTII, without wishing to be bound by theory, DMSO may be acting, at least in part, by altering the conversion of 3,3,1,0,0 to G0F by GnTII. Further, as shown in FIG. 2A, the presence of DMSO had a temporal effect on G0F levels, which declined over days 10, 12, and 14.

Figure 3A:
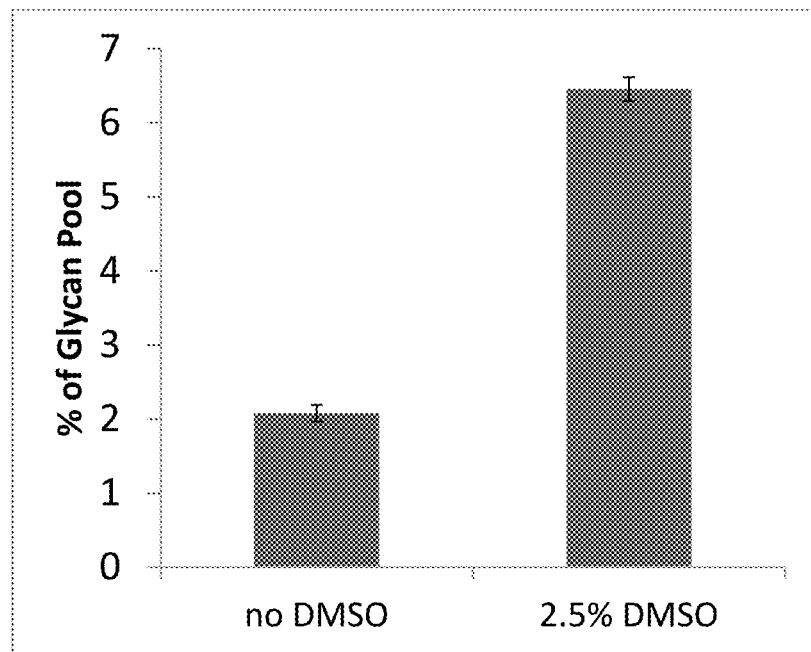
FIG. 3A is a graphic representation of total high mannose glycan levels in preparations of a model antibody from cells grown in medium with or without DMSO.
Figure 3B:
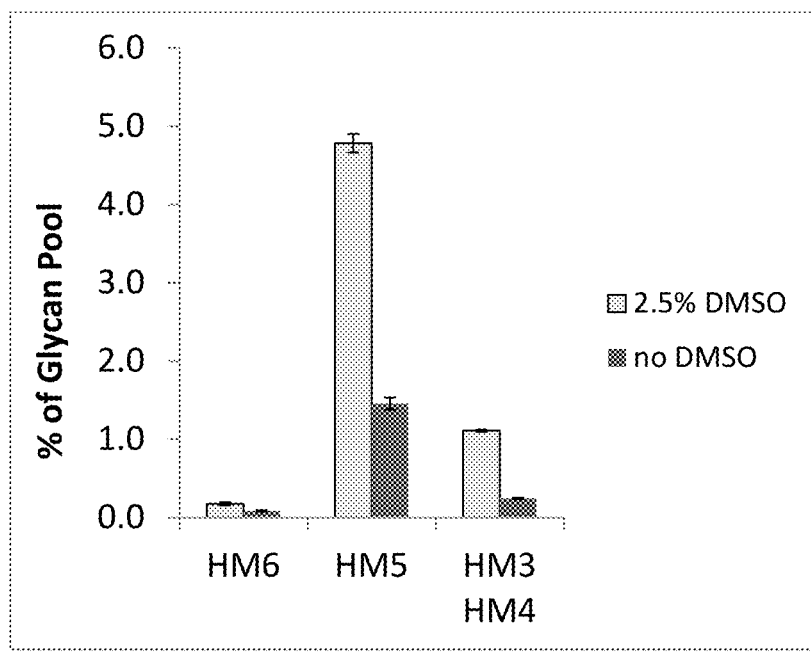
FIG. 3B is a graphic representation of high mannose 6 (HM6) glycan level, high mannose 5 (HM5) glycan level, or high mannose 3 and 4 (HM3 and HM4) glycan level in preparations of a model antibody from cells grown in medium with or without DMSO.

The impact of DMSO on high mannose glycans is shown in FIGS. 3A and 3B. As shown in FIG. 3A, DMSO increased the total level of high mannose glycans compared to no DMSO. Further, DMSO led to increased levels of high mannose 6, high mannose 3, and high mannose 5 glycans (see FIG. 3B).

Figure 4A:
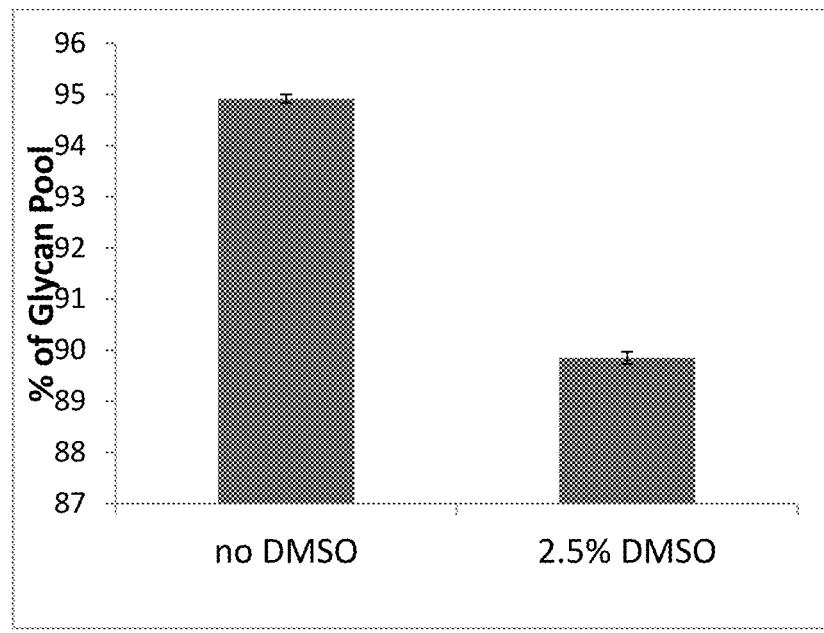
FIG. 4A is a graphic representation of fucosylated glycan levels in preparations of a model antibody from cells grown in medium with or without DMSO.
Figure 4B:
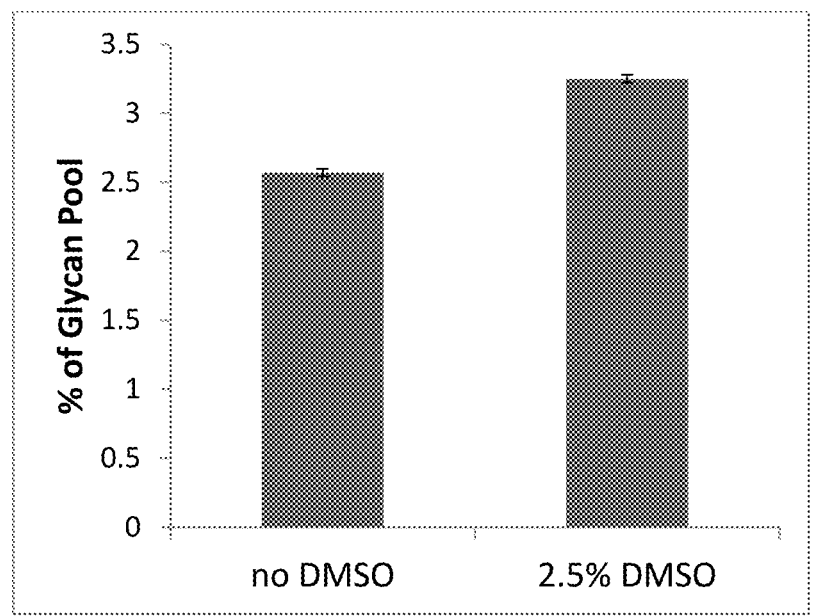
FIG. 4B is a graphic representation of afucosylated glycan levels in preparations of a model antibody from cells grown in medium with or without DMSO.
Figure 5A:
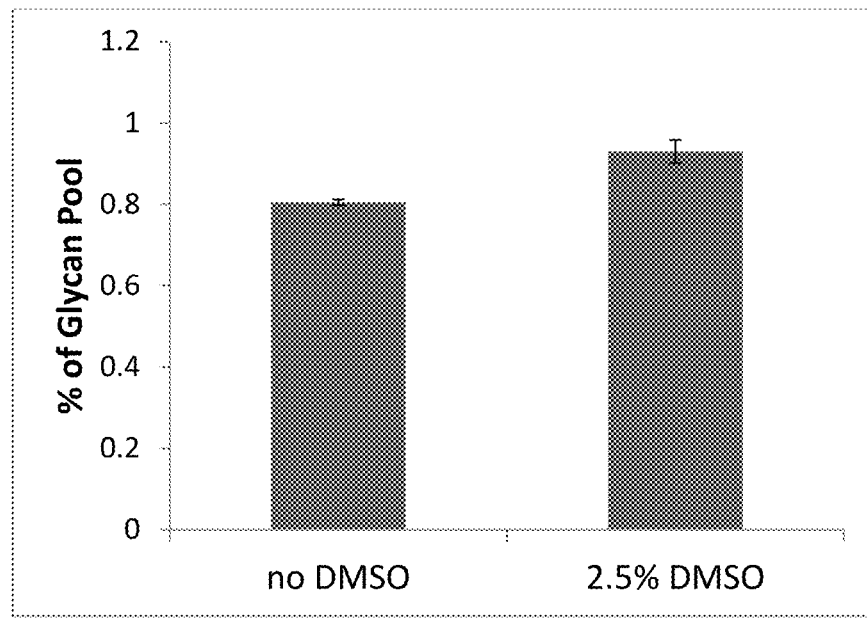
FIG. 5A is a graphic representation of total sialylated glycan levels in preparations of a model antibody from cells grown in medium with or without DMSO.
Figure 5B:
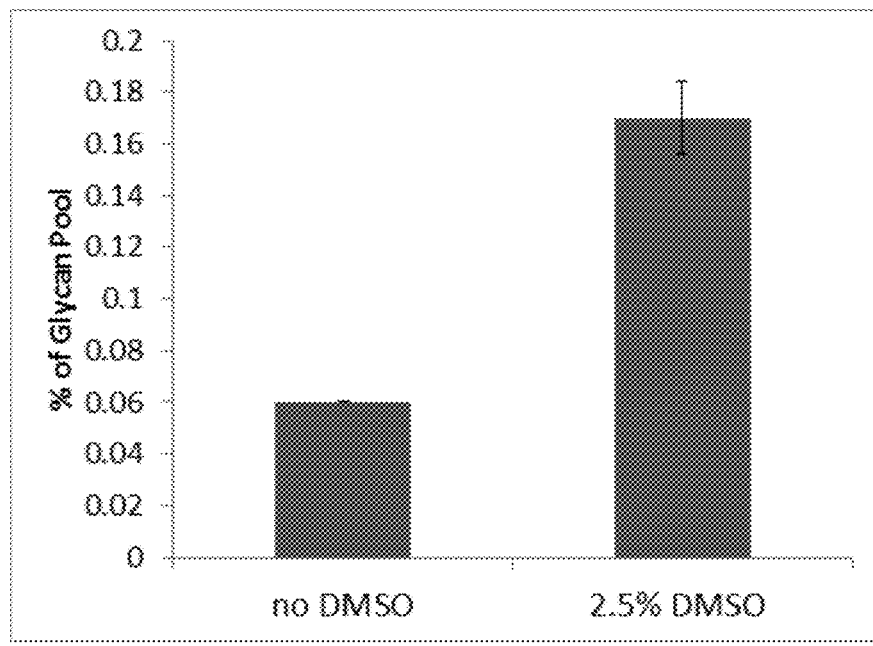
FIG. 5B is a graphic representation of 3,5,1,1,0 sialylated glycan levels in preparations of a model antibody from cells grown in medium with or without DMSO.
Figure 6:
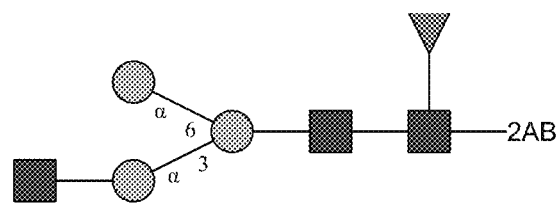
FIG. 6 depicts structural illustrations of 3,3,1,0,0 and 3,5,1,1,0 glycans (triangle=fucose; dark gray circles=mannose; squares=N-acetyl glucosamine; light gray circle (between square and diamond)=galactose; diamond=sialic acid). "2AB" is a dye conjugated to the end of the glycan that is linked to a polypeptide.
Figure 6:
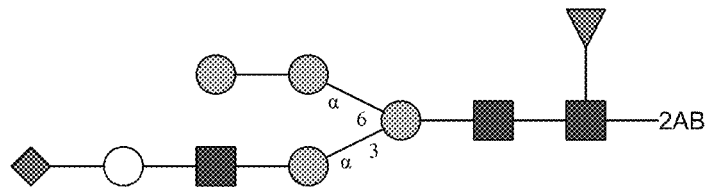

DMSO also affected the level of fucosylated glycans, resulting in a decreased level of fucosylated glycans (FIG. 4A), with an increase in afucosylated glycans (FIG. 4B). Further, DMSO resulted in an increase in sialylated glycans (FIG. 5A), with a specific increase in the level of 3,5,1,1,0 sialylated glycan (FIG. 5B; structure shown in FIG. 6).

This Example demonstrates that culturing cells in DMSO can be used to produce polypeptides, expressed by the cells, having particular levels of glycans.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of producing an adalimumab preparation, comprising:
   (a) providing a cell genetically engineered to express adalimumab; and
   (b) culturing the cell in a culture medium comprising dimethylsulfoxide (DMSO) under conditions in which the cell expresses adalimumab, to produce a preparation of adalimumab having a target value of one or more of high mannose and fucosylated glycans, wherein the target value of the high mannose glycans is 5% to 20% high mannose glycans and the target value of the fucosylated glycans is 70% to 100% fucosylated glycans.

2. The method of claim 1, further comprising harvesting the preparation of adalimumab.

3. The method of claim 2, further comprising formulating the preparation into a drug product.

4. The method of claim 1, wherein the target value is a predetermined pharmaceutical product specification.

5. The method of claim 1, further comprising evaluating the level of one or more of high mannose glycans and fucosylated glycans in the adalimumab preparation.

6. The method of claim 1, wherein the culture medium comprises 0.5% to 5% DMSO.

7. The method of claim 6, wherein the culture medium comprises 1% to 2% DMSO.

8. The method of claim 6, wherein the culture medium comprises 2% to 3% DMSO.

9. The method of claim 6, wherein the culture medium comprises 3% to 4% DMSO.

10. The method of claim 6, wherein the culture medium comprises 2% to 5% DMSO.

11. The method of claim 1, wherein the target value is 5% to 10% high mannose glycans.

12. The method of claim 1, wherein the target value is 10% to 20% high mannose glycans.

13. The method of claim 1, wherein the culturing step comprises a first stage and a second stage.

14. The method of claim 13, wherein the first stage comprises culturing the cell in the culture medium comprising a first level of DMSO, and the second stage comprises culturing the cell in the culture medium comprising a second level of DMSO.

15. The method of claim 14, wherein the first level of DMSO is no DMSO and the second level of DMSO is 1% to 5% DMSO.

16. The method of claim 15, wherein the first stage comprises culturing the cell in the first level of DMSO for 1 to 8 days.

17. The method of claim 16, wherein the second stage comprises culturing the cell in the second level of DMSO for 1 to 12 days.

18. The method of claim 1, wherein the cell is a CHO cell.

19. The method of claim 18, wherein the CHO cell is a CHO-K1 or CHO-DG44 cell.

20. A method of producing an adalimumab preparation, comprising:
   (a) providing a target value of one or more of high mannose glycans and fucosylated glycans;
   (b) culturing a cell genetically engineered to express adalimumab in a culture medium comprising DMSO, under conditions in which the cell expresses the adalimumab;
   (c) harvesting a preparation of the adalimumab produced by the cell; and
   (d) formulating the preparation into a drug product if the preparation meets the target value of the one or more of high mannose glycans and fucosylated glycans, wherein the target value of the high mannose glycans is 5% to 20% high mannose glycans and the target value of the fucosylated glycans is 70% to 100% fucosylated glycans.

21. The method of claim 20, further comprising evaluating the level of the one or more of high mannose glycans and fucosylated glycans in the adalimumab preparation.

22. The method of claim 20, wherein the target value is a predetermined pharmaceutical product specification.

23. The method of claim 20, wherein the culture medium comprises 0.5% to 5% DMSO.

24. The method of claim 23, wherein the culture medium comprises 1% to 2% DMSO.

25. The method of claim 23, wherein the culture medium comprises 2% to 3% DMSO.

26. The method of claim 23, wherein the culture medium comprises 3% to 4% DMSO.

27. The method of claim 23, wherein the culture medium comprises 2% to 5% DMSO.

28. The method of claim 20, wherein the target value is 5% to 10% high mannose glycans.

29. The method of claim 20, wherein the target value is 10% to 20% high mannose glycans.

30. The method of claim 20, wherein the culturing step comprises a first stage and a second stage.

31. The method of claim 30, wherein the first stage comprises culturing the cell in the culture medium comprising a first level of DMSO, and the second stage comprises culturing the cell in the culture medium comprising a second level of DMSO.

32. The method of claim 31, wherein the first level of DMSO is no DMSO and the second level of DMSO is 1% to 5% DMSO.

33. The method of claim 32, wherein the first stage comprises culturing the cell in the first level of DMSO for 1 to 8 days.

34. The method of claim 33, wherein the second stage comprises culturing the cell in the second level of DMSO for 1 to 12 days.

35. The method of claim 20, wherein the cell is a CHO cell.

36. The method of claim 35, wherein the CHO cell is a CHO-K1 or CHO-DG44 cell.

* * * * *